(12) United States Patent
Little et al.

(10) Patent No.: US 12,188,050 B2
(45) Date of Patent: Jan. 7, 2025

(54) KIDNEY ORGANOIDS AND METHODS OF MANUFACTURING

(71) Applicant: MURDOCH CHILDRENS RESEARCH INSTITUTE, Parkville (AU)

(72) Inventors: Melissa Little, Parkville (AU); Santhosh V. Kumar, Parkville (AU)

(73) Assignee: MURDOCH CHILDRENS RESEARCH INSTITUTE (AU)

( * ) Notice: Subject to any disclaimer, the term of this patent is extended or adjusted under 35 U.S.C. 154(b) by 660 days.

(21) Appl. No.: 16/759,642

(22) PCT Filed: Oct. 31, 2018

(86) PCT No.: PCT/AU2018/051178
§ 371 (c)(1),
(2) Date: Apr. 27, 2020

(87) PCT Pub. No.: WO2019/084612
PCT Pub. Date: May 9, 2019

(65) Prior Publication Data
US 2020/0291361 A1    Sep. 17, 2020

(30) Foreign Application Priority Data

Oct. 31, 2017    (AU) ............................. 2017904424

(51) Int. Cl.
| | | |
|---|---|---|
| C12N 5/071 | (2010.01) | |
| A61K 35/22 | (2015.01) | |
| A61L 27/38 | (2006.01) | |
| B33Y 70/00 | (2020.01) | |
| G01N 33/50 | (2006.01) | |

(52) U.S. Cl.
CPC ............ *C12N 5/0686* (2013.01); *A61K 35/22* (2013.01); *A61L 27/3804* (2013.01); *B33Y 70/00* (2014.12); *G01N 33/5014* (2013.01); *A61L 2430/26* (2013.01); *C12N 2501/119* (2013.01); *C12N 2501/415* (2013.01); *C12N 2506/45* (2013.01); *C12N 2513/00* (2013.01); *C12N 2533/30* (2013.01)

(58) Field of Classification Search
None
See application file for complete search history.

(56) References Cited

U.S. PATENT DOCUMENTS

| | | |
|---|---|---|
| 9,791,433 B2 | 10/2017 | Marx |
| 2016/0237409 A1 | 8/2016 | Little et al. |
| 2016/0264940 A1* | 9/2016 | Broly .................. C12N 5/0031 |
| 2018/0245050 A1* | 8/2018 | Freedman .............. A61K 35/44 |
| 2020/0157507 A1* | 5/2020 | Matsunaga ......... A61L 27/3882 |

FOREIGN PATENT DOCUMENTS

| | | |
|---|---|---|
| CN | 102725409 A | 10/2012 |
| WO | 2016094948 A1 | 6/2016 |
| WO | 2017049243 A1 | 3/2017 |

OTHER PUBLICATIONS

Morizane et al. "Nephron organoids derived from human pluripotent stem cells model kidney development and injury." Nature Biotechnology 33.11 (2015): 1193-1200. (Year: 2015).*
Pagliuca et al. "Generation of functional human pancreatic β cells in vitro." Cell 159.2 (2014): 428-439. (Year: 2014).*
Abbasalizadeh et al. "Bioprocess development for mass production of size-controlled human pluripotent stem cell aggregates in stirred suspension bioreactor." Tissue Engineering Part C: Methods 18.11 (2012): 831-851. (Year: 2012).*
Taguchi et al. "Redefining the in vivo origin of metanephric nephron progenitors enables generation of complex kidney structures from pluripotent stem cells." Cell stem cell 14.1 (2014): 53-67. (Year: 2014).*
Takasato et al. "Generation of kidney organoids from human pluripotent stem cells." Nature protocols 11.9 (Aug. 18, 2016): 1681-1692. (Year: 2016).*
Wu "Mechanisms of animal cell damage associated with gas bubbles and cell protection by medium additives." Journal of biotechnology 43.2 (1995): 81-94. (Year: 1995).*
Morizane, R , et al., "Nephron organoids derived from human pluripotent stem cells model kidney development and injury", Nature Biotechnology 33(11), 1193-1200 (2015).
Murphy, S , et al., "3D bioprinting of tissues and organs", Nature Biotechnolog 32(8), 773-785 (2014).
Patent Cooperation Treaty , International Searching Authority, Search Report and Written Opinion for PCT/AU2018/051178, 14 pages, Jan. 15, 2019.
Przepiorski, A , et al., "A simple bioreactor-based method to generate kidney organoids from pluripotent stem cells", Stem Cell Reports 11, 470-484 (2018).
Taguchi, A , et al., "Higher-order kidney organogenesis from pluripotent stem cells.", Cell Stem Cell 21, 730-746 (2017).
Takasato, M , et al., "Directing human embryonic stem cell differentiation towards a renal lineage generates a self-organizing kidney", Nature 16(1), 118-126 (2014).
Takasato, M , et al., "Kidney organoids from human iPS cells contain multiple lineages and model human nephrogenesis", Nature 526, 564-568 (2015).
Schutgens, F , et al., "Pluripotent stem cell-derived kidney organoids: An in vivo-like in vitro technology", European Journal of Pharmacology 790, 12-20 (2016).
Takasato, M, et al., "A strategy for generating kidney organoids: Recapitulating the development in human pluripotent stem cells", Developmental Biology 420, 210-220 (2016).

* cited by examiner

*Primary Examiner* — Emily A Cordas
(74) *Attorney, Agent, or Firm* — Viksnins Harris Padys Malen LLP

(57) ABSTRACT

The present disclosure relates to kidney organoids and methods of manufacturing the same. The organoids and methods may be used in a variety of applications such as disease modelling, drug screening, regenerative medicine and 5 scaling up production of kidney cells.

17 Claims, 13 Drawing Sheets

KIDNEY ORGANOIDS AND METHODS OF MANUFACTURING

FIELD OF THE INVENTION

Figure 1:
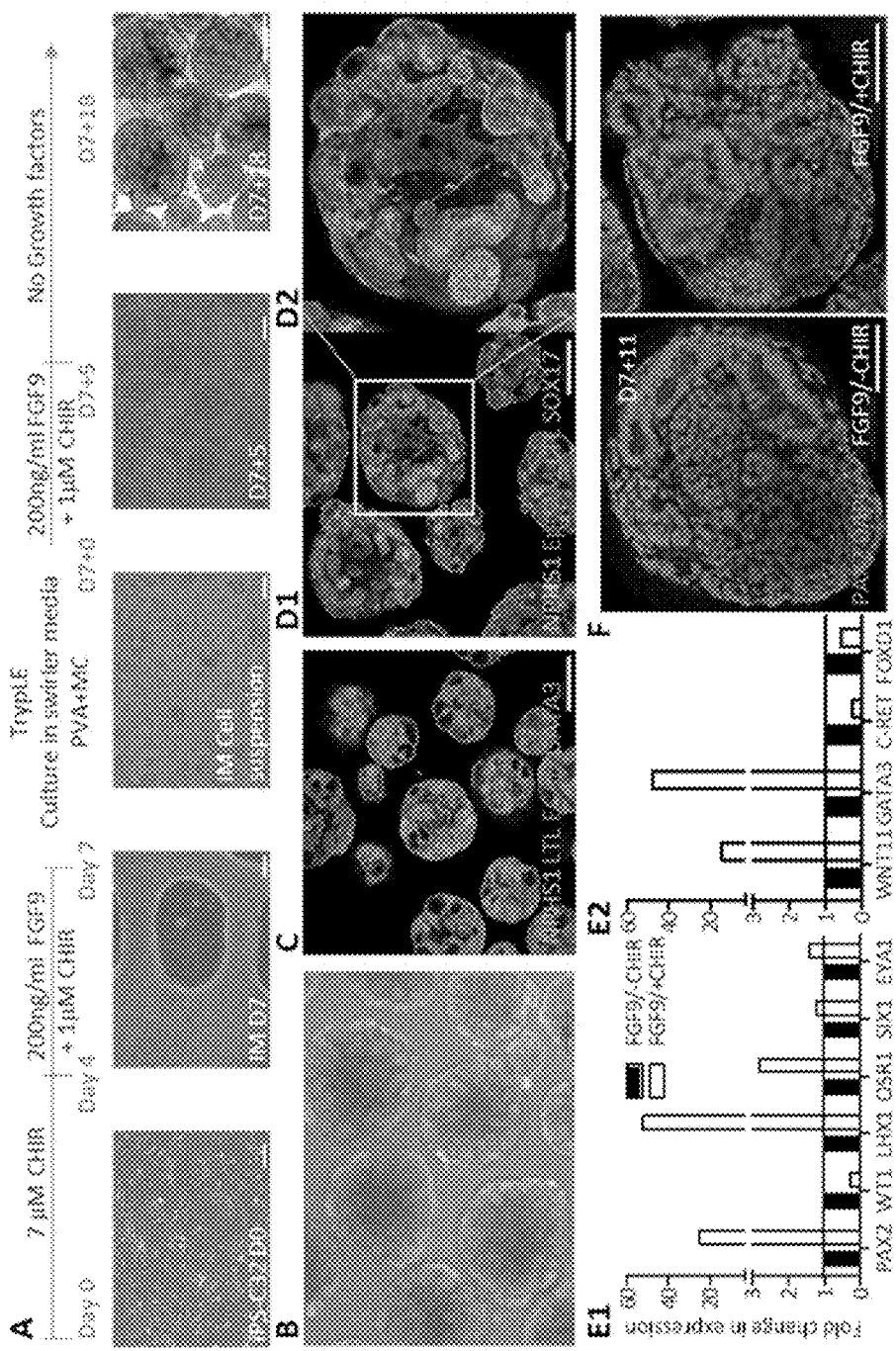

The present disclosure relates to kidney organoids and methods of manufacturing the same. The organoids and methods may be used in a variety of applications such as disease modelling, drug screening, regenerative medicine and scaling up production of kidney cells.

BACKGROUND OF THE INVENTION

Kidneys play a major role in removal of waste products and maintain body fluid volume. The functional working units are known as nephrons. The human kidneys contains up to 2 million epithelial nephrons responsible for blood filtration all of which arise after birth. No nephron progenitors exist in the postnatal human kidney. This absence of progenitor population ensures no ability for nephron self-renewal and therefore, subsequent injury, aging and disease can lead to end stage renal disease (ESDR). The limited treatment options used for the treatment of ESDR generally places additional stress to the already damaged kidney. The only available but costly treatment options at the late stages of kidney disease is dialysis and/or kidney transplantation both of which have significant disadvantages and affect the quality of life of the patient.

The directed differentiation of human pluripotent stem cells (hPSCs), including both human embryonic stem cells (hES) and human induced pluripotent stem cells (hiPS), to distinct cellular endpoints has enabled the generation of organoid models of a variety of human tissues, including the kidney. Previous organoid models such as those discussed in Takasato et al. (2015) Nature, Vol. 526:564-568 are expensive and may produce organoids having a complex three dimensional structure, restricting their use in imaging and screening applications. These organoids may also be subject to diffusion limitations after three weeks in culture, limiting their capacity to generate increased cell numbers and their capacity to mature. This in turn makes current protocols for kidney organoid production a suboptimal source of cells for regenerative medicine or disease modelling. New kidney organoids and methods for their manufacture are therefore required.

SUMMARY OF THE INVENTION

The present inventors have surprisingly identified kidney organoids having a simplified three dimensional structure. Such organoids are advantageous as they are easier to image and culture long term. Accordingly, in an example, the present disclosure encompasses a kidney organoid comprising less than 50 nephrons. In another example, the kidney organoid comprises less than 25 nephrons. In another example, the kidney organoid comprises less than 15 nephrons. In another example, the kidney organoid comprises between 5 and 12 nephrons. In an example, kidney organoids are produced by swirling a population of intermediate mesoderm (IM) cells in a cell culture medium under conditions sufficient to promote kidney organoid development. In this example, the IM cell culture medium may comprise about 180 to 220 ng/ml FGF9.

In an example, kidney organoids are produced by swirling between $0.5 \times 10^6$ and $1.5 \times 10^6$ IM cells/ml. In another example, kidney organoids are produced by swirling about 0.8 to $1.2 \times 10^6$ IM cells/ml. In another example, the kidney organoid comprises cells expressing high levels of nephron markers. In another example, the kidney organoid comprises cells expressing high levels of any one or more of PAX2, LHX1, SIX1, OSR1, WNT11 and GATA3. In another example, the kidney organoid comprises cells expressing high levels of PAX2, LHX1, SIX1, OSR1, WNT11 and GATA3. In another example, the kidney organoid comprises cells expressing high levels of any one or more of PAX2, SIX1, LHX1, OSR1, WNT11, GATA3, PAX8, EYA1 and CITED1 and/or low levels of any one or more of PDGFRA, MEIS2, WT1 and/or C-RET. In another example, the kidney organoid comprises cells expressing high levels of PAX2, LHX1, SIX1, OSR1, WNT11, GATA3, PAX8, EYA1 and CITED1.

In another example, the kidney organoid is derived from stem cells selected from the group consisting of H9, hES3, iPSC GAPTrap Id-Tomato, CRL1502.C32, CLR1502.3, hES3 SOX17mCherry or H9 GAPTrap Luc2.

In another example, the kidney organoid comprises cells expressing low levels of stromal markers. In another example, the kidney organoid comprises cells expressing low levels of PDGFRA, MEIS2, WT1 and/or C-RET. In another example, the kidney organoid comprises NPHS+ podocytes, LTL+ proximal segments, ECAD+ distal segments, ECAD+/GATA3+ collecting duct or a combination thereof. In another example, the kidney organoid comprises from about $1 \times 10^4$ to $5 \times 10^4$ cells. In another example, the kidney organoid comprises about $1.5 \times 10^4$ to $2.5 \times 10^4$ cells. In another example, the kidney organoid has a diameter of about 250 to 500 μm. In another example, the kidney organoid remains viable in swirler culture for at least eighteen days. In another example, the kidney organoid remains viable in swirler culture for at least three weeks. In another example, the kidney organoid remains viable in swirler culture for at least four weeks. In another example, the kidney organoids nephrons comprise collecting duct (GATA3+; ECAD+), early distal tube (GATA3−; LTL−; ECAD+), early proximal tube (LTL+; ECAD−) and glomerulus (WT1+).

The present inventors have also surprisingly identified that cells of kidney organoids disclosed herein continue to divide after 7 days in swirler culture (e.g. D7+7). Without wishing to be bound by any particular theory, this may indicate that organoids produced using swirler culture are more suitable for therapeutic applications such as transplantation.

In another example, the present disclosure encompasses a composition which comprises a kidney organoid defined herein. In another example, the present disclosure encompasses a composition which comprises a kidney organoid defined herein or a digest thereof. For example, the present disclosure encompasses a composition which comprises a kidney organoid defined herein or an enzymatic digest thereof.

Again, without wishing to be bound by any particular theory, it is thought that the low complexity of kidney organoids disclosed herein may render them more suitable for producing compositions for transplantation. For example, compositions produced from low complexity kidney organoids may be more inclined to differentiate into correct cell types rather than form teratomas or cartilage. In another example, the present disclosure encompasses a composition which comprises an enzymatic digestion of a kidney organoid defined herein.

In another example, the present disclosure encompasses a method of treating kidney disease comprising, administering a composition defined herein to a subject in need thereof. In an example, the composition comprises a whole organoid. In another example, the composition comprises a digest of an organoid disclosed herein. For example, the kidney disease may be kidney failure. In an example, the composition is administered intravenously. In another example, the composition is administered via renal artery injection, renal parenchymal injection, implantation or subcapsular transplantation.

In another example, the present disclosure encompasses an in-vitro method of producing a kidney organoid, the method comprising, swirling a population of intermediate mesoderm (IM) cells in a cell culture medium comprising FGF.

In an example, the method provides a cost-effective means for scaling-up production of kidney cell types in vitro. In an example, the IM cells are swirled in culture medium containing FGF, CHIR and heparin. In an example, IM cells are swirled in culture for at least 5 days, wherein the first 24 hours comprise swirling cells in a cell culture medium comprising FGF, heparin, CHIR and ROCK inhibitor and the next four days comprise culturing cells in a cell culture medium comprising FGF, heparin and CHIR. In this example, ROCK inhibitor is present in the cell culture medium for the first 24 hours and is absent from the cell culture medium for the following days. In an example, the cell culture mediums comprise from 100 to 300 ng/ml FGF9. In an example, the cell culture mediums comprise from 180 to 220 ng/ml FGF9. In an example, the cell culture mediums comprise PVA and MC. In an example, the first 24 hours comprise swirling cells in a cell culture medium comprising FGF, 0.5 to 1.5 µg/ml heparin, 0.5 to 1.5 µM CHIR and 9 to 11 µM ROCK inhibitor. In another example, the next four days comprise swirling cells in a cell culture medium comprising FGF, 0.5 to 1.5 µg/ml heparin and 0.5 to 1.5 µM CHIR. In this example, ROCK inhibitor is absent from the cell culture medium for the next four days. In another example, the next four days comprise culturing cells in a cell culture medium comprising FGF9, heparin, CHIR, MC and PVA. In another example, the next four days comprise culturing cells in a cell culture medium comprising FGF9, heparin, CHIR, 0.05 to 0.2% MC and 0.05 to 0.2% PVA. In another example, the remaining days in culture, after the at least five days, the cells are cultured in a cell culture medium comprising 0.05 to 1.5% PVA and 0.05 to 1.5% MC. In this example, the cell culture medium may contain PVA and MC without FGF9, heparin, CHIR or ROCK inhibitor. In another example, the cell culture mediums comprising FGF comprise at least 100 ng/ml FGF9. In another example, the cell culture mediums comprising FGF comprise at least 150 ng/ml FGF9. In another example, the cell culture mediums comprising FGF comprise 150 to 250 ng/ml FGF9. In another example, the cell culture mediums comprising FGF comprise 180 to 220 ng/ml FGF9.

In some examples, the methods of producing kidney organoids disclosed herein result in improved cell yield compared with cell yield obtained from organoids produced without swirling such as those described in Takasato et al. (2015). In an example, a 30 fold increase in cell yield from the starting number of IM cells added to swirler culture may be observed after 10 days in swirler culture. In another example, a 35 fold increase in cell yield from the starting number of IM cells added to swirler culture may be observed after 10 days in swirler culture. In another example, a 40 fold increase in cell yield from the starting number of IM cells added to swirler culture may be observed after 12 days in swirler culture. In another example, a 45 fold increase in cell yield from the starting number of IM cells added to swirler culture may be observed after 12 days in swirler culture. In another example, a 30 to 40 fold increase in cell yield from the starting number of IM cells added to swirler culture may be observed after 12 days in swirler culture. In another example, a 30 to 40 fold increase in cell yield from the starting number of IM cells added to swirler culture may be observed after 18 days in swirler culture.

In an example, the IM cells are swirled between 30 and 90 rpm. In another example, the IM cells are swirled for 18 to 24 days.

In another example, the IM cells are produced by culturing a population of stem cells for at least seven days, wherein the first 4 to 5 days comprise culturing stem cells in a cell culture medium comprising at least 6 µM of a Wnt/β-catenin agonist and the remaining days in culture comprises culturing cells in a cell culture medium comprising FGF and at least 0.5 µM of a Wnt/β-catenin agonist. In an example, the Wnt/β-catenin agonist is CHIR. In these examples, the cell culture medium comprising FGF may comprise between 100 to 300 ng/ml of FGF9. In these examples, the cell culture medium comprising FGF may comprise between 0.5 to 1.5 µM CHIR. In these examples, the cell culture medium comprising FGF may further comprise 0.5 to 1.5 µg/ml heparin. In an example, the IM cells are dissociated with EDTA or trypsin or TrypLE™ select and passed through a mesh screen before swirling. In an example, the stem cells are pluripotent stem cells, embryonic stem cells or induced pluripotent stem (iPS) cells. In an example, the stem cells are selected from the group consisting of H9, hES3, iPSC GAPTrap Id-Tomato, CRL1502.C32, CLR1502.3, hES3 SOX17mCherry or H9 GAPTrap Luc2.

The present inventors identified that the methods of the present disclosure require relatively low starting cell numbers. This is advantageous as it allows for cost effective scale up of organoid and cell culture. Accordingly, in another example, the methods of the present disclosure comprise swirling a population of from $0.5 \times 10^6$ IM cells/ml to $3 \times 10^6$ IM cells/ml. In another example, the methods of the present disclosure comprise swirling a population of about $0.8 \times 10^6$ IM cells/ml to $1.2 \times 10^6$ IM cells/ml. Accordingly, in an example, the present disclosure encompasses a kidney organoid disclosed herein, wherein the organoid is produced by swirling a population of IM cells. Exemplary timing and culture media used for swirling the population of IM cells to produce a kidney organoid are disclosed herein. In an example, the organoid is produced by swirling an IM cell population which comprises from $0.5 \times 10^6$ IM cells/ml to $3 \times 10^6$ IM cells/ml. In another example, the organoid is produced by swirling an IM cell population which comprises less than $2 \times 10^6$ IM cells. In another example, the organoid is produced by swirling an IM cell population which comprises from $0.5 \times 10^6$ IM cells/ml to $1.5 \times 10^6$ IM cells/ml. In another example, the organoid is produced by swirling an IM cell population which comprises about $0.8 \times 10^6$ IM cells/ml to $1.2 \times 10^6$ IM cells/mi.

In another example, the present disclosure encompasses a kidney organoid produced by a method defined herein.

In another example, the present disclosure encompasses a method of screening a candidate compound for nephrotoxicity, the method comprising contacting a kidney organoid defined herein with a candidate compound to determine whether or not the candidate compound is nephrotoxic. In an example, the candidate compound is a small molecule.

In another example, the present disclosure encompasses a kidney organoid, cell population or composition defined herein when used for producing a kidney, or kidney cells or tissues. In another example, the present disclosure encompasses a kidney organoid, cell population or composition defined herein for use in treating kidney disease. In some examples, a cell population refers to the cells derived from enzymatic digestion of a kidney organoid.

The present inventors have also surprisingly identified that culturing stem cells in medium comprising a low concentration of CHIR and activating Wnt/β-catenin signalling for a long duration is beneficial in producing improved intermediate mesoderm.

In one example, the present disclosure encompasses an in-vitro method of producing intermediate mesoderm (IM) cells, the method comprising, culturing a population of posterior primitive streak (PPS) cells for 2 to 5 days in a cell culture medium comprising FGF and less than 4 μM of a Wnt/β-catenin agonist.

In another example, stem cells can be initially cultured in CHIR for around seven days wherein the stem cells are cultured in culture medium comprising high concentration CHIR for the first 4 to 5 days before being cultured in culture medium comprising low concentration CHIR and FGF for the remaining days. Accordingly, in another example, the present disclosure encompasses an in-vitro method of producing intermediate mesoderm (IM) cells, the method comprising, culturing a population of stem cells for at least seven days, wherein the first 4 to 5 days comprise culturing stem cells in a cell culture medium comprising at least 6 μM of a Wnt/β-catenin agonist and the remaining days in culture comprises culturing cells in a cell culture medium comprising FGF and at least 0.5 μM of a Wnt/β-catenin agonist. In an example, the remaining days in culture comprises culturing cells in a cell culture medium comprising FGF that comprises between 0.5 and 3 μM of a Wnt/β-catenin agonist. In another example, the remaining days in culture comprises culturing cells in a cell culture medium comprising FGF that comprises 0.8 to 1.2 μM of a Wnt/β-catenin agonist. In another example, the first 4 days comprise culturing stem cells in a cell culture medium comprising at least 6 μM of a Wnt/β-catenin agonist. In another example, the first 4 days comprise culturing stem cells in a cell culture medium comprising 7 μM of a Wnt/β-catenin agonist. In an example, the cell culture medium comprising FGF comprises between 100 to 300 ng/ml FGF9. In an example, the cell culture medium comprising FGF comprises between 180 to 220 ng/ml FGF9. In another example, the cell culture medium comprising FGF9 further comprises heparin. For example, the cell culture medium may comprise at least 1.0 μg/ml heparin. In an example, the stem cells are pluripotent stem cells, embryonic stem cells or induced pluripotent stem (iPS) cells. In another example, the stem cells are selected from the group consisting of H9, hES3, iPSC GAPTrap Id-Tomato, CRL1502.C32, CLR1502.3, hES3 SOX17mCherry or H9 GAPTrap Luc2.

In another example, the present disclosure encompasses a method of bio-printing a kidney comprising preparing a bioink from an organoid or cell population defined herein and bio-printing a kidney. In some examples, a cell population refers to the cells derived from enzymatic digestion of a kidney organoid.

In another example, the present disclosure encompasses an organoid, composition or cell population defined herein when used for producing a kidney, or kidney cells or tissues. In another example, the present disclosure encompasses a method of generating nephron cell types for cellular therapy, the method comprising producing a kidney organoid using a method or population of IM cells defined herein.

Any example herein shall be taken to apply mutatis mutandis to any other example unless specifically stated otherwise.

The present disclosure is not to be limited in scope by the specific examples described herein, which are intended for the purpose of exemplification only. Functionally-equivalent products, compositions and methods are clearly within the scope of the disclosure, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The disclosure is hereinafter described by way of the following non-limiting Examples and with reference to the accompanying drawings.

BRIEF DESCRIPTION OF THE ACCOMPANYING DRAWINGS

FIG. 1. Generation of kidney micro-organoids in suspension culture. (A) Outline of the kidney micro-organoid differentiation protocol with images from a differentiation performed using CRL1502.C32 cells. (B) Bright field images showing uniform kidney micro-organoids on Day 7+18 (scale 100 mm). (C, D1 and D2) Immunofluorescence and confocal images of micro-organoids showing formation of nephron segments independent of micro-organoid size and shape, including development of vascular structures (scale 100 mm). (E) Bar graphs showing average fold change for intermediate mesoderm gene expression profiling by qPCR on Day 7+0 for FGF9+/−1 μM CHIR99021. The data represented as Mean, (F) Immunofluorescence for PAX2 for FGF9+/−1 μM CHIR99021 treatment (scale 50 μm) (D7+11). (G) Immunofluorescence and confocal images of nephron compartments within kidney micro-organoids; podocytes (NPHS1+ and MAFB+), proximal tubules (LTL+, CUBN+, LRP2+ and HNF4A+), distal tubules (ECAD), collecting duct (ECAD+ GATA3+) and endothelial cells (SOX17+ and PECAM1+) (scale 50 μm).

Figures 1, 2:
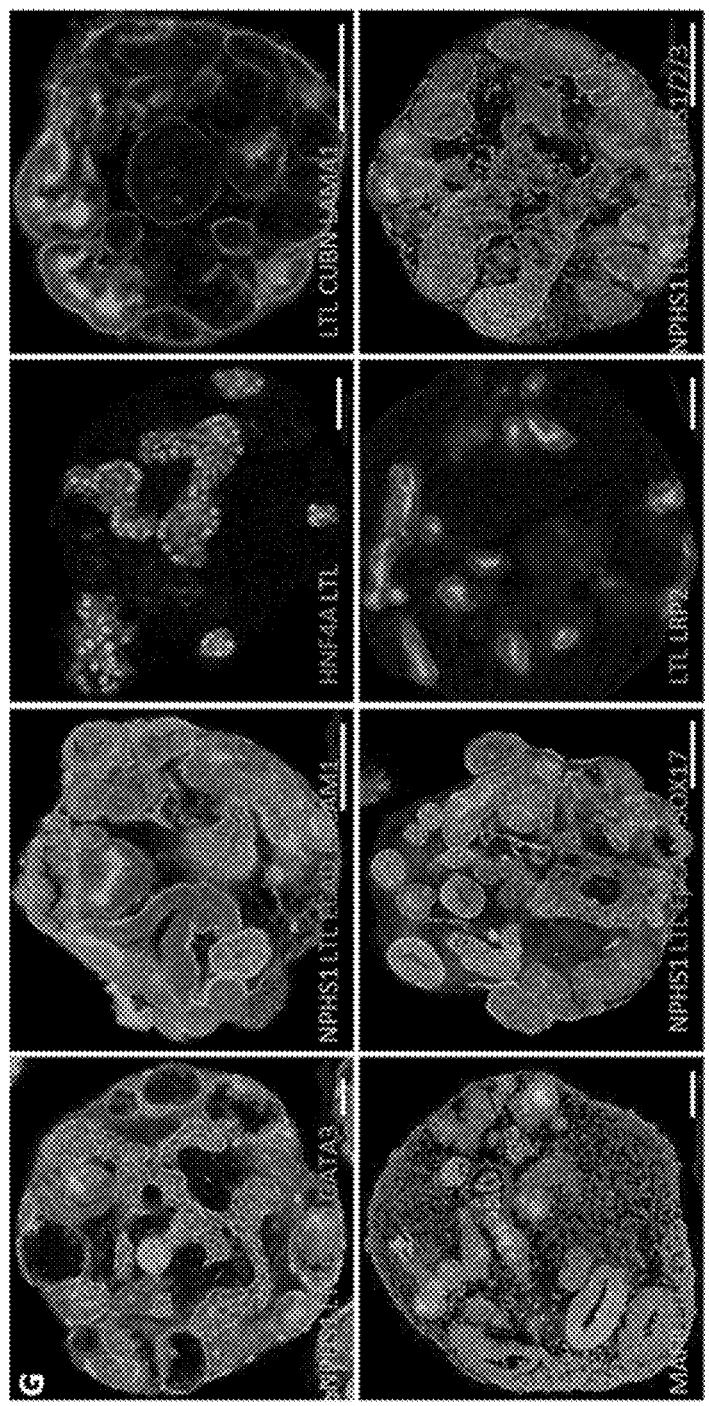
Figure 2:
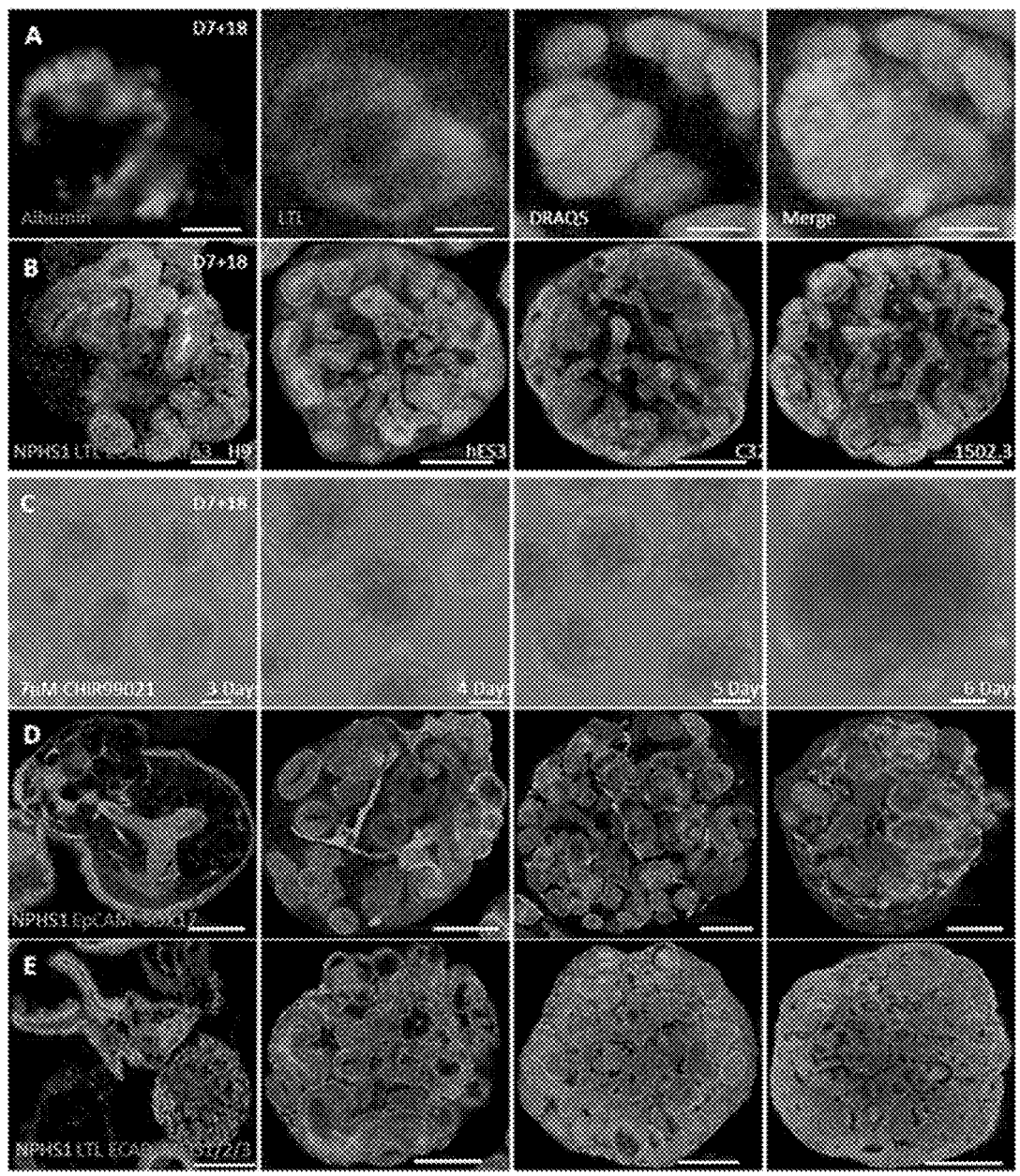

FIG. 2. Micro-kidney organoids in suspension culture shows functional proximal tubules and initial Wnt signalling is important for kidney organoid development and maturation. (A) Confocal image of micro-kidney organoid tubules on Day 7+18 showing FITC albumin uptake (scale 5 μm). (B) Confocal images of micro-kidney organoids generated using 4 different cell lines, including hES (H9 GAP-Trap Luc2, hES3 SOX17mCherry) and iPS (CRL1502.C32 and CRL1502.3) on Day 7+18 with antibodies labelling different nephron segments (scale 50 μm). (C, D and E) hES3 SOX17mCherry derived micro-organoids generated after exposure to different days of initial 7 μM CHIR99021 for 3, 4, 5 and 6 days treatment showing bright field (C, scale 100 μm) and immunofluorescence confocal images showing SOX17+ vasculature (D) and MEIS1/2/3+ stroma (E) (scale 100 μm).

Figures 1, 3:
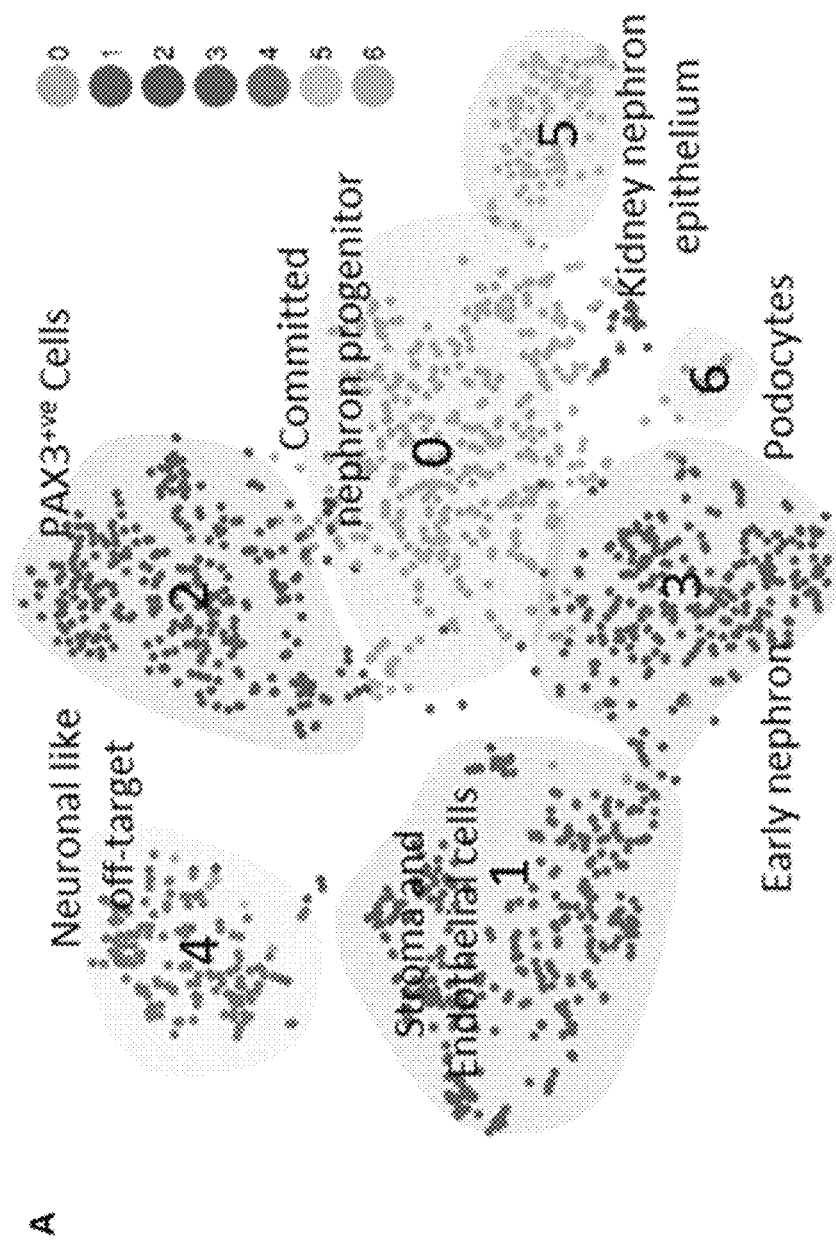
Figures 2, 3:
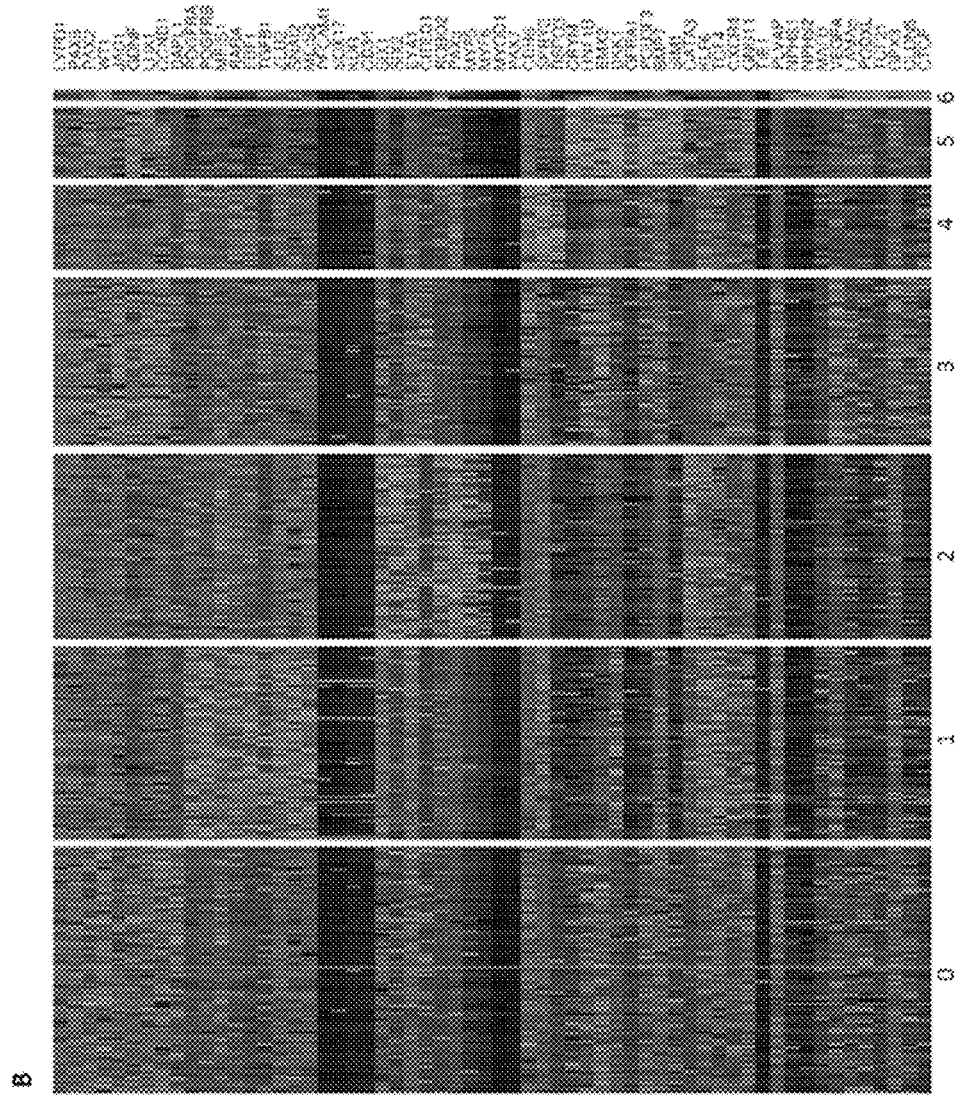
Figure 3:
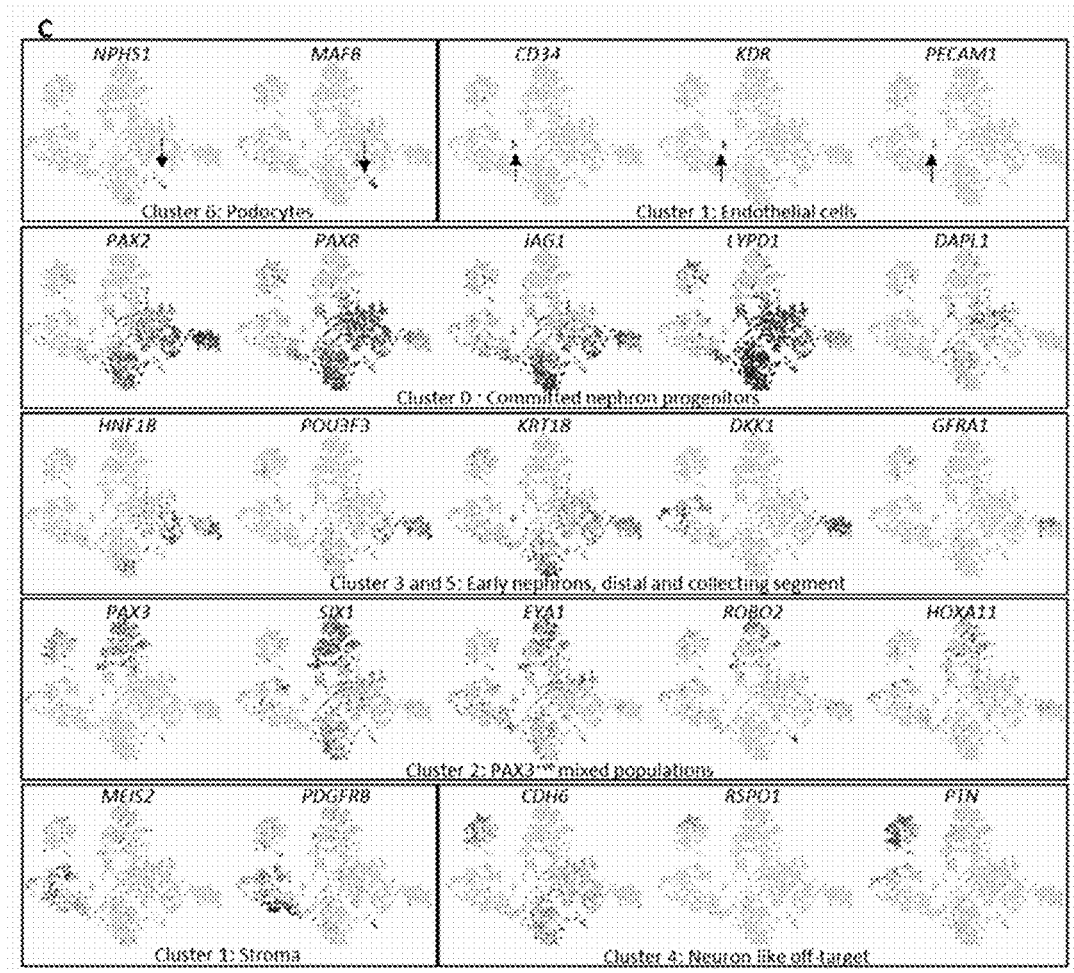

FIG. 3. Transcriptional validation of kidney differentiation within micro-organoids. (A) t-SNE plot after Seurat™ clustering of single cell RNA-seq of Day 7+18 CRL1502-C32 micro-organoids showing 11 different clusters. (B) Heat-map showing scaled gene expression of key marker genes within clusters. (C) t-SNE plots indicating the expression of key marker genes for selected nephron cell type. Colour intensity is scaled per gene, with blue indicating higher expression.

Figures 1, 4:
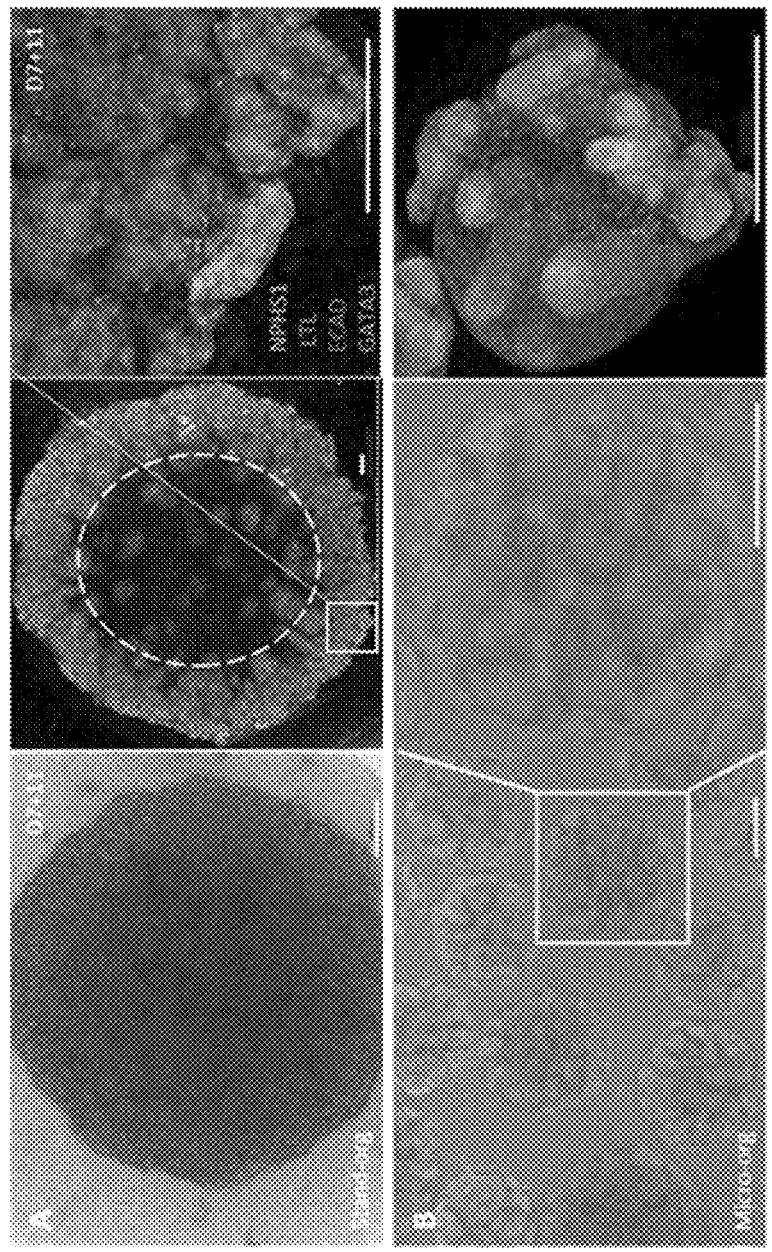
Figures 2, 4:
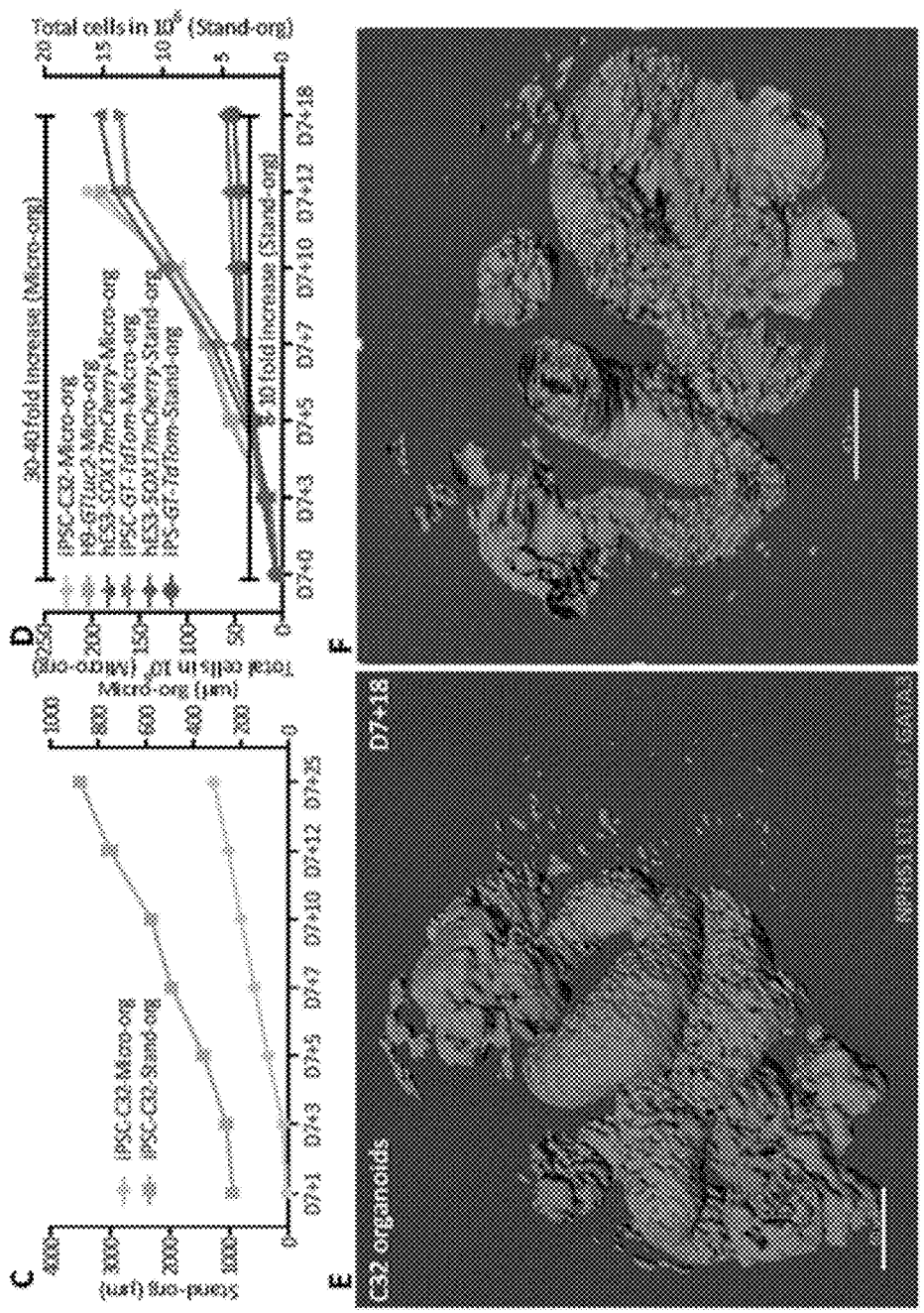

FIG. 4. Kidney micro-organoids provides a better platform for efficient hPSC-derived kidney cell scale-up. (A) Bright-field image of standard kidney organoid at Day 7+11 (left, scale 500 µm), immunofluorescence and confocal image (tile scan) of entire standard organoid showing the spatial restriction of nephron structures to the edge of the organoid (middle scale 200 µm) and magnified image of a nephron within that organoid (right, scale 200 µm). (B) Bright-field image of kidney micro-organoid and magnified bright-field image of a single kidney micro-organoids, confocal image of kidney micro-organoids at D7+11 (scale 200 µm). (C) Change in size of the organoids at different stages of development. (D) Change in total cell number from starting cell number over time and scalable capacity of micro-organoids compare to standard organoid. (E-F) Immunofluorescence and Bitplane-Imaris™ 3D reconstruction of C32 micro-organoids at D7+18 showed clear nephron segments connected to each other in a polarized manner starting from glomeruli (NPHS1), proximal tubule (LTL+), distal tubules (ECAD+), collecting duct (ECAD+, GATA3+) and interstitial cells (GATA3+).

Figures 1, 5:
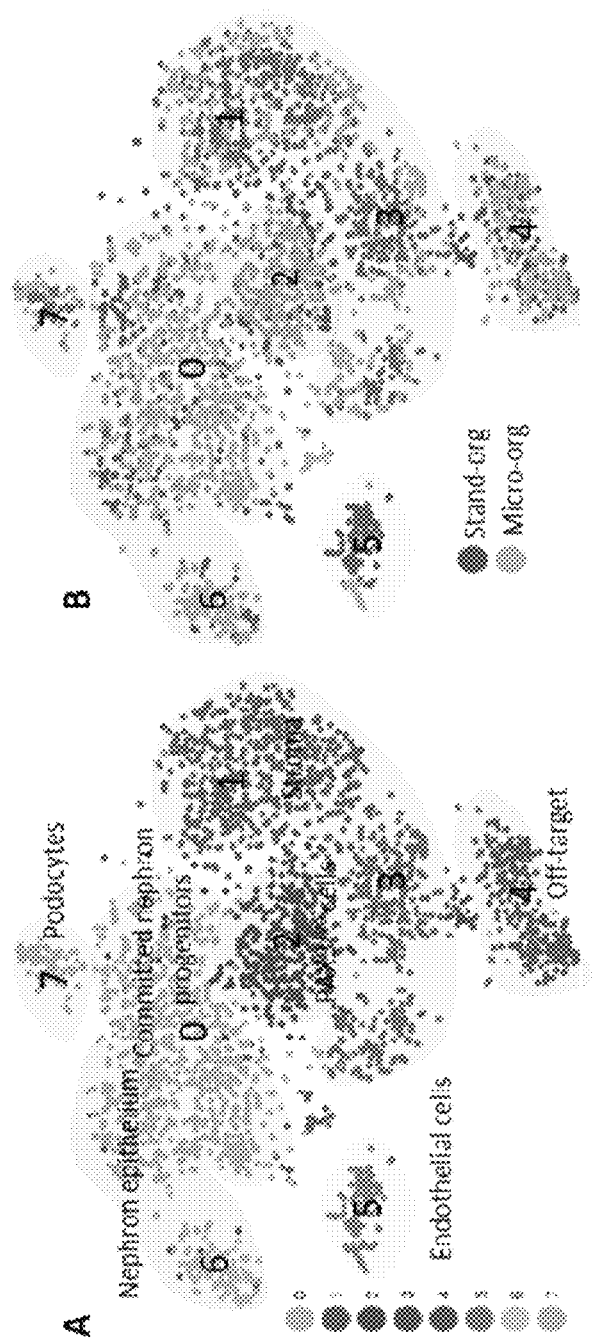
Figures 2, 5:
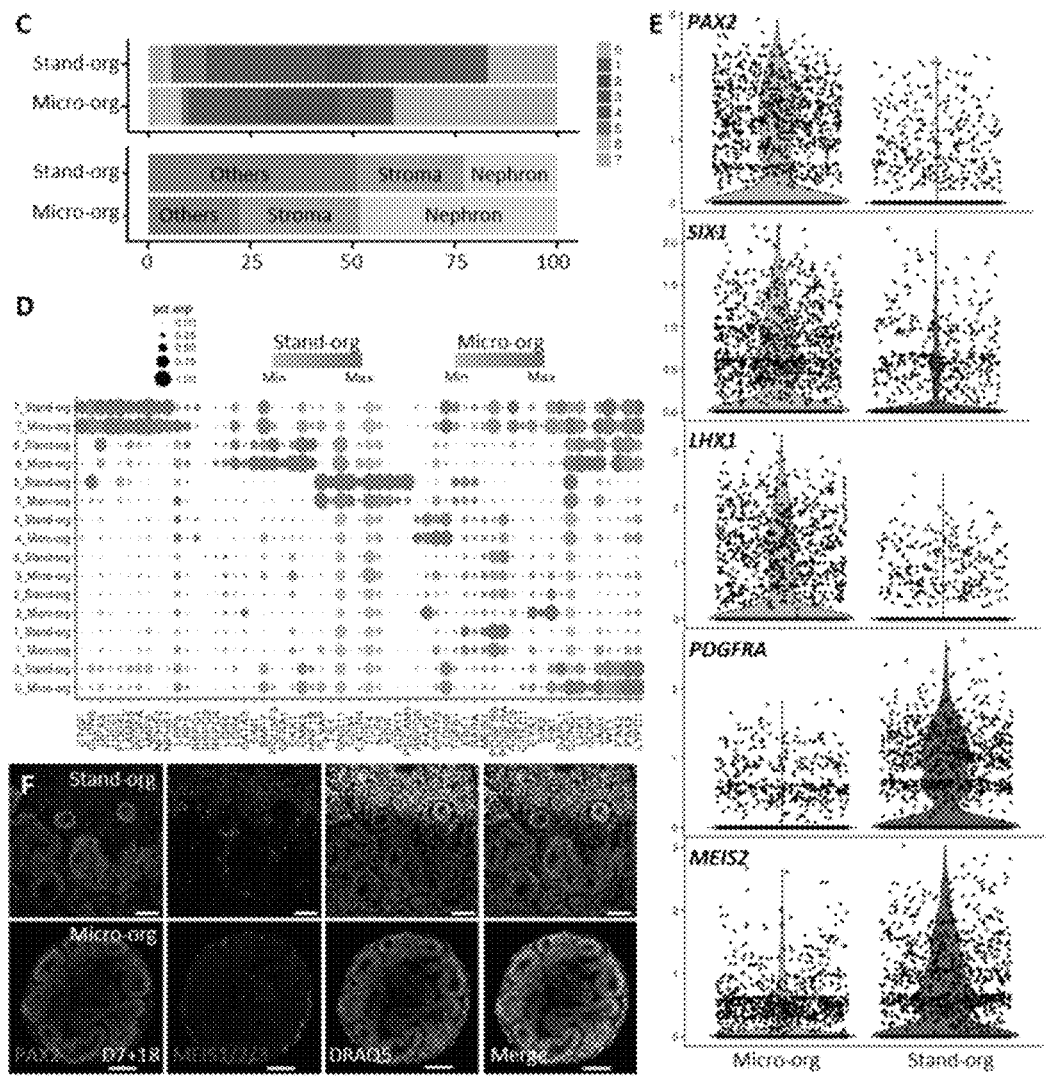

FIG. 5. Comparative single cell transcriptional profiling of standard kidney organoids and micro-organoids demonstrates an equivalent nephrogenic patterning. (A) t-SNE plots after integrated Seurat™ analysis of kidney micro-organoid (Micro-org) and standard organoid (Stand-org) 10x scRNA-Seq data from on Day 7+18 (CRL1502.32). (B) t-SNE plot representing micro-organoid and standard organoid contributions to cell types in each cluster, coloured by organoid type (C) Bar graph representing the proportion of each of the Micro-org or Stand-org datasets assigned to each transcriptional cluster and differentiation lineage type. (D) Split dot plots showing the gene expression of kidney markers in each cluster between kidney micro-organoids and standard organoid. (E) Violin and scatter plots showing the log-normalised counts per cell for nephron (PAX2, SIX1, LHX1) and stromal related genes (PDGFRA, MEIS2) within Micro-org and Stand-org. (F) Immunofluorescence showing the expression of PAX2 and MEIS1/2/3 between kidney Micro-org and Stand-org (scale 50 µm).

Figure 6:
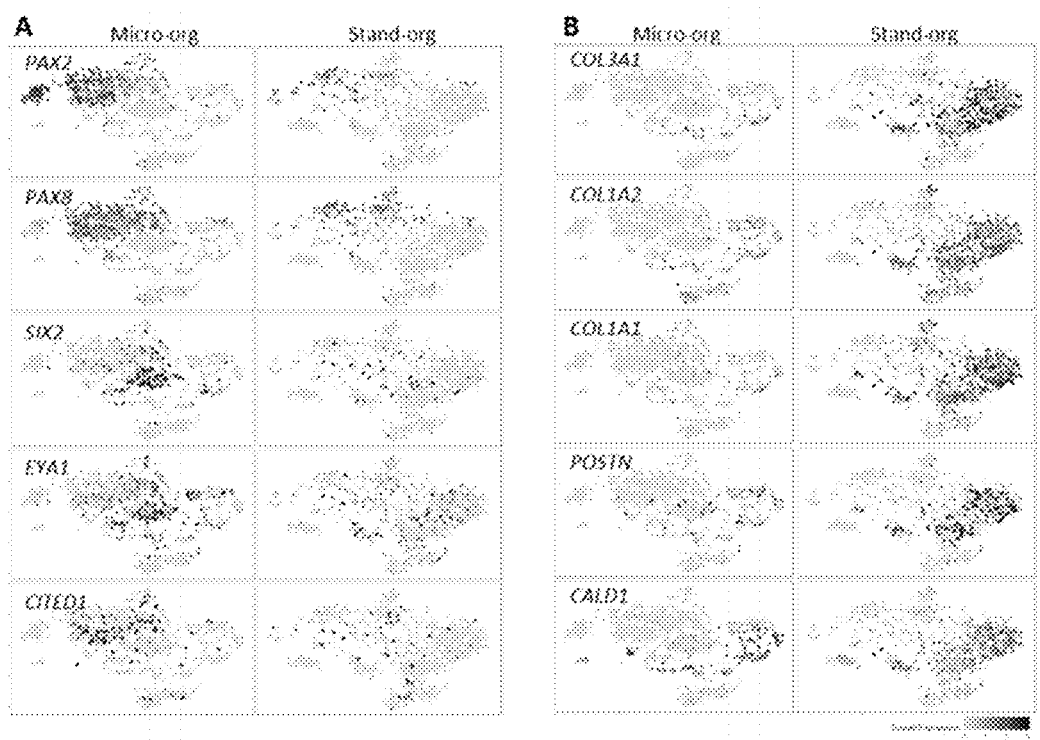

FIG. 6. Comparison of nephron and stromal markers within micro and stand-org. (A and B) t-SNE feature plots for nephron and stromal genes in standard and micro-organoid scRNA-Seq data.

Figure 7:
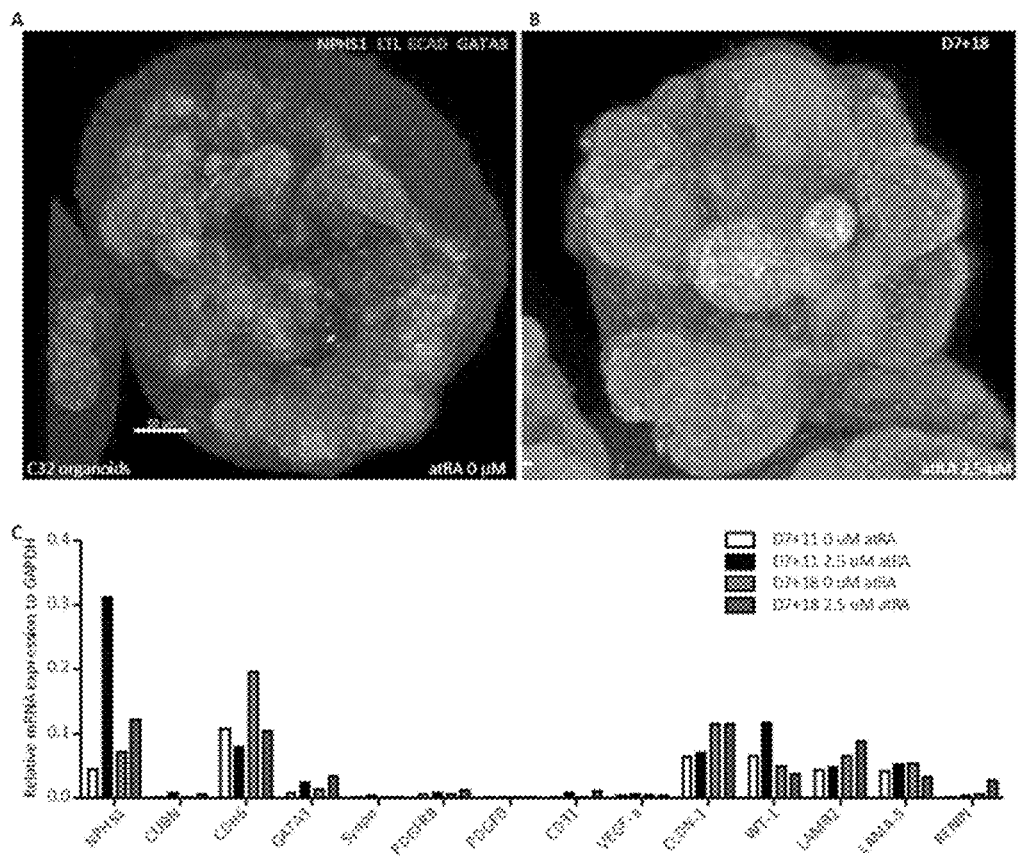

FIG. 7. All Trans-Retinoic Acid helps in the improvement of glomerular maturation in kidney micro-organoids. Immunofluorescence analysis of C32 swirler organoids generated by swirler suspension culture. (A) Organoids generated without supplementation at atRA. (B) Organoids generated with atRA from D7+5 to D7+10 show improved glomerular podocyte maturation. (C) qPCR analysis of organoids generated with and without atRA at different time points (D7+11 and D7+18).

Figure 8:
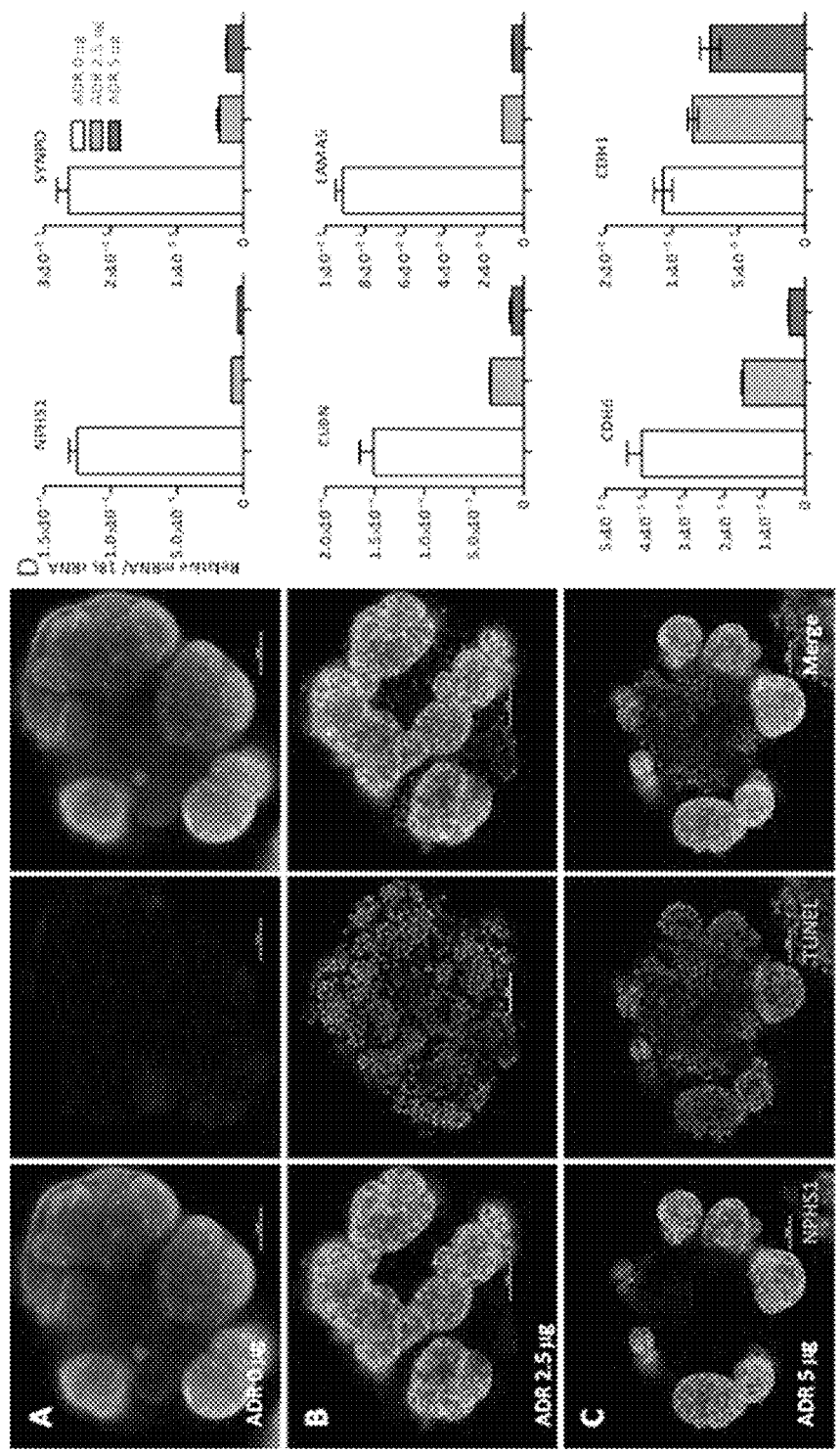

FIG. 8. Kidney micro-organoids provides a platform for drug toxicity screening. Adriamycin treatment for (24 hours) induces dose dependent toxicity on kidney micro-organoids (A-C) by increasing the expression of TUNEL an apoptotic marker. (D) Adriamycin treatment also reduces the expression of kidney specific genes in micro-organoids.

DETAILED DESCRIPTION OF THE INVENTION

Unless specifically defined otherwise, all technical and scientific terms used herein shall be taken to have the same meaning as commonly understood by one of ordinary skill in the art (e.g., molecular biology, cell culture, stem cell differentiation, cell therapy, genetic modification, disease modelling, biochemistry, physiology, and clinical studies).

Unless otherwise indicated, the molecular and statistical techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), J. E. Coligan et al. (editors) Current Protocols in Immunology, John Wiley & Sons (including all updates until present), Michos Odysse (editor) Kidney Development: Methods and Protocols (Springer), Robert Lanza (editor) Handbook of Stem Cells, Volume 1, Embryonic Stem Cells (Elsevier).

As used in this specification and the appended claims, terms in the singular and the singular forms "a," "an" and "the," for example, optionally include plural referents unless the content clearly dictates otherwise. Thus, for example, reference to "a kidney organoid" optionally includes one or more kidney organoid.

As used herein, the term "about", unless stated to the contrary, refers to +/−10%, more preferably +/−5%, more preferably +/−1%, of the designated value.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Various subjects can be administered cell compositions according to the present disclosure. In an example, the subject is a mammal. The mammal may be a companion animal such as a dog or cat, or a livestock animal such as a horse or cow. In another example, the subject is a human. Terms such as "subject", "patient" or "individual" are terms that can, in context, be used interchangeably in the present disclosure.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease are mitigated or eliminated. In an example, the term "treatment" refers to both therapeutic treatment and prophylactic or preventative measures for kidney disease, anemia, EPO deficiency, tubular transport deficiency, or glomerular filtration deficiency wherein the object is to reverse, prevent or slow down (lessen) the targeted disorder. Those in need of treatment include those already having a kidney disease, anemia, EPO deficiency, tubular transport deficiency, or glomerular filtration deficiency, those prone to having such disorders or those in whom such disorders are to be prevented. In an example, treatment encompasses stabilization and/or improvement of kidney function.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is used to refer to an amount necessary to effect treatment of a kidney disorder or condition as hereinbefore described. The effective amount may vary according to the disease or condition to be treated and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner. The effective amount can be administered in a single dose or in a dose repeated once or several times over a treatment period.

A "therapeutically effective amount" is at least the minimum concentration required to effect a measurable improvement of a particular kidney disorder (e.g. Nephritis, renal cell carcinoma). A therapeutically effective amount herein may also vary according to factors such as the disease state, age, sex, and weight of the patient, and the ability of the cellular composition to elicit a desired response in the individual. A therapeutically effective amount is also one in which any toxic or detrimental effects of the composition are outweighed by the therapeutically beneficial effects. In the case of renal cell carcinoma, a therapeutically effective amount can reduce the number of cancer cells; reduce the primary tumour size; inhibit (i.e., slow to some extent and, in some examples, stop) cancer cell infiltration into peripheral organs; inhibit (i.e., slow to some extent and, in some examples, stop) tumour metastasis; inhibit or delay, to some extent, tumour growth or tumour progression; and/or relieve to some extent one or more of the symptoms associated with the renal cell carcinoma. For renal cell carcinoma therapy, efficacy in vivo can, for example, be measured by assessing the duration of survival, time to disease progression (TTP), the response rates (RR), duration of response, and/or quality of life.

By "intermediate mesoderm (IM)" cells is meant embryonic mesodermal cells that arise from definitive mesoderm which in turn is derived from posterior primitive streak and can ultimately develop into the urogenital system, inclusive of the ureter and kidney and other tissues such as gonad. Non-limiting examples of markers characteristic or representative of intermediate mesoderm include PAX2, OSR1 and/or LHX1.

It will also be appreciated that production of IM cells is not meant to imply that the IM cells are a pure or homogeneous population of IM cells without other cell types being present (such as definitive mesoderm). Accordingly, reference to "IM cells" or a "population of IM cells" means that the cells or cell population comprise(s) IM cells.

Suitably, according to the invention IM cells are produced by contacting posterior primitive streak cells with one or more agents that facilitate differentiation of the posterior primitive streak cells into IM cells, as will be described in more detail hereinafter. Preferably, the IM cells are produced by contacting posterior primitive streak cells with one or more agents that facilitate differentiation of the posterior primitive streak cells into IM cells By "posterior primitive streak (PPS)" cells is meant cells obtainable from, or cells functionally and/or phenotypically corresponding to, cells of the posterior end of a primitive streak structure that forms in the blastula during the early stages of mammalian embryonic development. The posterior primitive streak establishes bilateral symmetry, determines the site of gastrulation and initiates germ layer formation. Typically, posterior primitive streak is the progenitor of mesoderm (i.e presumptive mesoderm) and anterior primitive streak is the progenitor of endoderm (i.e presumptive endoderm). Non-limiting examples of markers characteristic or representative of posterior primitive streak include Brachyury (T). A non-limiting example of a marker characteristic or representative of anterior primitive streak is SOX17. MIXL1 may be expressed by both posterior and anterior primitive streak.

It will also be appreciated that production of posterior primitive streak cells is not meant to imply that the posterior primitive streak cells are a pure or homogeneous population of posterior primitive streak cells without other cell types being present. Accordingly, reference to "posterior primitive streak cells" or a "population of posterior primitive streak cells" means that the cells or cell population comprise(s) posterior primitive streak cells.

Posterior primitive streak cells are produced by contacting hPSC cells with one or more agents that facilitate differentiation of the hPSC cells into posterior primitive streak cells, as will be described in more detail hereinafter. For example, the one or more agents may include bone morphogenic protein 4 (BMP4), Activin A and/or a Wnt agonist such as CHIR99021.

Kidney Organoid

The present disclosure encompasses the production of intermediate mesoderm (IM) cells. The term "intermediate mesoderm (IM)" is used in the context of the present disclosure to refer to embryonic mesodermal cells that arise from definitive mesoderm which in turn is derived from posterior primitive streak and can ultimately develop into the urogenital system, inclusive of the ureter and kidney and other tissues such as gonad. Non-limiting examples of markers characteristic or representative of intermediate mesoderm include PAX2, OSR1 and/or LHX1.

In an example, culture conditions are provided to allow these IM cells to 'self-organise' and form kidney organoids. The term "kidney organoid" is used in the context of the present disclosure to refer to a heterogeneous 3D agglomeration of cells that recapitulates aspects of cellular self-organization, architecture and signalling interactions present in the native kidney. Examples of kidney organoids are described in Takasato et al. (2015) Nature, Vol. 526:564-568, WO 2014/197934 and WO 2016/094948. The terms "renal organoid" and "kidney organoid" can be used interchangeably in the context of the present disclosure.

The present inventors have surprisingly identified kidney organoids having a simplified three dimensional structure. Such organoids are advantageous as they are easier to image and culture long term. For example, a healthy adult has 0.8 to 2 million nephrons in each kidney, typically around 1 million. In contrast, an organoid encompassed by the present disclosure comprises much lower nephron numbers. Accordingly, in one example, the present disclosure encompasses a kidney organoid comprising architectural hallmarks of a native kidney with reduced numbers of nephrons. In an example, a kidney organoid encompassed by the present disclosure can comprise one or more nephrons. In an example, nephron(s) segment into distal and proximal tubules, early loops of Henle, and glomeruli. In another example, organoids comprise segmented nephrons surrounded by endothelial cells, perivascular cells and renal interstitium. In another example, organoids of the present disclosure do not show the presence of vasculature.

In other examples, organoids according to the present disclosure are at least partially vascularised. For example, organoids can comprise nephrons containing podocytes elaborating foot processes and undergoing vascularisation.

In an example, kidney organoids are characterised in terms of % nephron, % stroma and/or % vasculature. In this example, kidney organoids can be characterised using single cell RNA sequencing. An example of single cell sequencing is provided below. In an example, kidney organoids comprise at least 20% mature nephron. In another example, kidney organoids comprise at least 25% mature nephron. In another example, kidney organoids comprise at least 30% mature nephron. In another example, kidney organoids comprise at least 31% mature nephron. In another example, kidney organoids comprise at least 32% mature nephron. In these examples, the kidney organoids also comprise at least 15% stroma. In another example, the kidney organoids also comprise at least 20% stroma. In another example, the kidney organoids also comprise at least 25% stroma. In another example, the kidney organoids do not comprise any substantial vasculature. In another example, the kidney organoids do not comprise vasculature.

In an example, kidney organoids according to the present disclosure comprise less than 100 nephrons. In another example, kidney organoids according to the present disclosure comprise less than 90, less than 80, less than 70, less than 60 nephrons. In another example, kidney organoids according to the present disclosure comprise less than 50 nephrons. In another example, kidney organoids according to the present disclosure comprise less than 40, less than 30, less than 20, less than 10 nephrons. In another example, kidney organoids according to the present disclosure comprise less than 5 nephrons. In another example, kidney organoids according to the present disclosure comprise less than 4, less than 3 nephrons.

In another example, kidney organoids according to the present disclosure comprise between 2 and 100 nephrons. In another example, kidney organoids according to the present disclosure comprise between 2 and 50 nephrons. In another example, kidney organoids according to the present disclosure comprise between 2 and 10 nephrons. In another example, kidney organoids according to the present disclosure comprise between 5 and 12 nephrons. In another example, kidney organoids according to the present disclosure comprise between 6 and 10 nephrons. In another example, kidney organoids according to the present disclosure comprise between 2 and 6 nephrons. In another example, kidney organoids according to the present disclosure comprise between 2 and 4 nephrons.

"Nephrons" are the functional working units of kidney which play a major role in removal of waste products from blood/plasma and maintenance of body fluid volume. They can be identified and counted in organoids disclosed herein by those of skill in the art using various methods. For example, nephrons can be visualized and counted using confocal microscopy and immunofluorescence labelling (e.g. WT1+ glomerulus; NPHS+ podocytes, LTL+ECAD− proximal tubule, ECAD+ distal tubule and ECAD+GATA3+ collecting duct).

Generally, the species identity of kidney organoids encompassed by the present disclosure, whether it is mammalian, such as mouse, human or otherwise is dictated by the cells used to generate the kidney organoid. In one example, the present disclosure encompasses mammalian kidney organoids. In this example, mammalian pluripotent stem cells are used to generate the kidney organoid. Mammalian kidney organoids may be representative of kidney from a companion animal such as a canine or feline, or a livestock animal such as an equine or a bovinae. Thus, in these examples, stem cells from canines, felines etc. are used to generate the kidney organoid. In another example, the mammalian kidney organoids are representative of kidney from mouse or rat. In another example, the kidney organoids are representative of kidney from higher order primates such as cynomolgus monkey or rhesus monkey. In another example, the mammalian kidney organoids are representative of kidney from humans. Where pluripotent stem cells from a particular species are used to generate a kidney organoid, the resulting kidney organoid may be identified based on that species. For example, when using human stem cells to generate a kidney organoid, the resulting kidney organoid can be identified as a human kidney organoid. Thus, in an example, kidney organoids encompassed by the present disclosure include human kidney organoids derived from human stem cells. Various other examples of stem cells that are suitable for generating kidney organoids are discussed below.

In another example, kidney organoids can be characterised based on expression of molecular markers. Marker expression can be characterised using various techniques such as immunohistochemistry or fluorescent activated cell sorting. Immunohistochemistry generally involves using a primary antibody specific for the marker of interest. Binding of the primary antibody to a marker can be visualised via various known methods. For example, a labelled secondary antibody that recognises the primary antibody can be used. In this example, the label could be an enzyme such as horse radish peroxidase, a radioactive isotope, a fluorescent reporter, an electro-chemiluminescent tag. Binding of the labelled secondary antibody to the primary antibody can be detected via cytological assessment or via an automated plate reader.

In a particular example, a kidney organoid or section or sample thereof is contacted with a specific primary antibody. The kidney organoid or section or sample thereof is then washed to remove any unbound primary antibody and then a secondary antibody specific for the primary antibody and linked to a peroxidase enzyme is applied to the sample. The kidney organoid or section or sample thereof is then washed to remove any unbound secondary antibody and 3,3'-Diaminobenzidine (DAB) is applied to the sample. The conversion of DAB into a coloured product is visualised by routine cytological assessment with the presence of a coloured product indicating that the marker is present in the sample. In an example, the level of coloured product may be quantified using Image J or various other software packages that are commercially available from suppliers such as Perkin Elmer and Leica.

In another example, a cell suspension is produced from a representative kidney organoid, a population thereof or section or sample thereof. Cells in suspension are contacted with a fluorescently labelled antibody that is specific for a particular maker. Cells positive for a particular marker are identified using techniques such as fluorescent activated cells sorting (FACS).

A cell that is referred to as being "positive" for a given marker may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively low or very low level by that cell or population, and that it generates a very low signal when detectably labelled or is undetectable above background levels, e.g., levels detected using an isotype control antibody.

In an example, markers of kidney organoids described herein can be detected using a fluorescent reporter gene. For example, expression of particular markers can be monitored to track development of kidney organoids or cells comprising the same in real time. For example, stem cells can be genetically engineered to express one or more fluorescent or chemiluminescent reporter(s) under a given set of conditions. Reporters can be used to track cell identity, cell viability or cell function in real time.

An example of a suitable reporter gene is exemplified below where a knock-in iPSC line is generated that harbours the mTagBFP2 fluorescent reporter gene inserted at the start codon of the endogenous MAFB locus ($MAFB^{mTagBFP2/+}$). MAFB is highly expressed in developing podocytes and therefore, expression of MAFB can be monitored to track development of podocytes in kidney organoids in real time. Other examples of reporter cell lines suitable for use in the methods disclosed herein include GATA3mCherry, RETtdTOMATO or Six2Cre.

In another example, kidney organoids comprise cells expressing high levels of one or more nephron markers. In another example, kidney organoids comprise cells expressing high levels of one or more of PAX2, SIX1, LHX1, OSR1, WNT11, GATA3, PAX8, EYA1 and CITED1. For example, kidney organoids can express high levels of PAX2. In another example, kidney organoids can express high levels of SIX1. In another example, kidney organoids can express high levels of LHX1. In another example, kidney organoids can express high levels of OSR1. In another example, kidney organoids can express high levels of WNT11. In another example, kidney organoids can express high levels of GATA3. In another example, kidney organoids comprise cells expressing high levels of PAX2, SIX1, LHX1, OSR1, WNT11 and GATA3. In another example, kidney organoids comprise cells expressing high levels of PAX2, SIX1, LHX1, OSR1, WNT11, GATA3, PAX8, EYA1 and CITED1. In these examples, kidney organoids can express high levels of a referenced marker such as one or more of PAX2, SIX1, LHX1, OSR1, WNT11, GATA3, PAX8, EYA1 and CITED1 relative to a kidney organoid with at least 100 nephrons. In another example, kidney organoids can express high levels of a referenced marker such as one or more of PAX2, SIX1, LHX1, OSR1, WNT11, GATA3, PAX8, EYA1 and CITED1 relative to a kidney organoid with more than 50 nephrons. In another example, kidney organoids can express high levels of a referenced marker such as one or more of PAX2, SIX1, LHX1, OSR1, WNT11 and GATA3 relative to kidney organoids which comprise at least $1 \times 10^5$ cells. In another example, kidney organoids can express high levels of a referenced marker such as one or more of PAX2, SIX1, LHX1, OSR1, WNT11 and GATA3 relative to kidney organoids which comprise at least $1 \times 10^6$ cells. In another example, kidney organoids can express high levels of a referenced marker such as one or more of PAX2, SIX1, LHX1, OSR1, WNT11 and GATA3 relative to kidney organoids produced without swirling such as those described in Takasato et al. (2015).

In another example, kidney organoids comprise cells expressing low levels of WT1. In another example, kidney organoids comprise cells expressing low levels of C-RET. In another example, kidney organoids comprise cells expressing low levels of FOXD1. In another example, kidney organoids comprise cells expressing low levels of PDGFRA. In another example, kidney organoids comprise cells expressing low levels of MEIS2. In another example, kidney organoids comprise cells expressing low levels of WT1 and C-RET. In another example, kidney organoids comprise cells expressing low levels of WT1, C-RET and FOXD1. In these examples, kidney organoids can express low levels of a referenced marker such as one or more of WT1, C-RET and FOXD1 relative to a kidney organoid with at least 100 nephrons. In another example, kidney organoids can express low levels of a referenced marker such as one or more of WT1, C-RET and FOXD1 relative to a kidney organoid with more than 50 nephrons.

In another example, kidney organoids comprise cells expressing high levels of PAX2, SIX1, LHX1, OSR1, WNT11 and GATA3 and low levels of WT1, C-RET, PDGFRA, MEIS2 and FOXD1. In another example, kidney organoids comprise cells expressing high levels of PAX2, SIX1, LHX1, OSR1, WNT11, GATA3, PAX8, EYA1 and CITED1 and low levels of WT1, C-RET, PDGFRA, MEIS2 and FOXD1.

In the above examples, high and low levels of expression are relative to kidney organoids cultured without swirling such as those described in Takasato et al. (2015) Nature, Vol. 526:564-568. In this example, high expression is at least 1 fold higher. In another example, high expression is at least 1.5 fold higher. In another example, high expression is at least 2 fold higher. In an example, low expression is at least 1 fold lower. In another example, low expression is at least 1.5 fold lower. In another example, low expression is at least 2 fold lower.

Expression levels can be measured using techniques such as polymerase chain reaction comprising appropriate primers for markers of interest. For example, total RNA can be extracted from organoids before being reverse transcribed and subject to PCR and analysis.

In an example, kidney organoids comprise nephron(s) comprising one or more of WT1+ glomerulus, NPHS+ podocytes, LTL+ECAD− proximal tubule, ECAD+ distal tubule and ECAD+GATA3+ collecting duct. In another example, kidney organoids comprise nephron(s) comprising NPHS+ podocytes, LTL+ proximal segments, ECAD+ distal segments and ECAD+GATA3+ collecting duct. Kidney organoids comprising above exemplified components can be identified in various ways. In one example, kidney organoids can be fixed and whole mounted before being visually assessed using confocal microscopy and immunofluorescence labelling.

In an example, kidney organoids can be characterised based on one or more of the above referenced markers after use in a method of screening discussed below. In another example, kidney organoids representative of a broader population can be characterised based on one or more of the above referenced markers before selecting kidney organoids expressing appropriate markers for use in a method of screening discussed below. For example, a population of kidney organoids can be produced using methods disclosed herein. Expression of one or more of the above markers can be confirmed in kidney organoids from the population before kidney organoids are selected for use in a method of screening discussed below.

In another example, organoids according to the present disclosure comprise between $0.5 \times 10^4$ and $8 \times 10^4$ cells. In another example, kidney organoids comprise between $0.8 \times 10^4$ and $7 \times 10^4$ cells. In another example, organoids according to the present disclosure comprise between $1 \times 10^4$ and $5 \times 10^4$ cells. In another example, organoids according to the present disclosure comprise at least $1 \times 10^4$ cells. In another example, organoids according to the present disclosure comprise less than $3 \times 10^4$ cells. In another example, organoids according to the present disclosure comprise $2 \times 10^4$ to $2.5 \times 10^4$ cells.

In another example, organoids according to the present disclosure have a diameter less than 2,500 μm. In another example, organoids according to the present disclosure have a diameter less than 2,000 μm. In another example, organoids according to the present disclosure have a diameter less than 1,000 μm. In another example, organoids according to the present disclosure have a diameter less than 500 μm. In another example, organoids according to the present disclosure have a diameter less than 400 μm. In another example, organoids according to the present disclosure have a diameter less than 300 μm. In another example, organoids according to the present disclosure have a diameter of 150 to 600 μm. In another example, organoids according to the present disclosure have a diameter of 200 to 500 μm. For example, organoids according to the present disclosure can have a diameter between 200 μm and 2,000 μm. In another example, organoids according to the present disclosure can have a diameter between 200 μm and 1,000 μm. In another example, organoids according to the present disclosure can have a diameter between 200 μm and 400 μm. In another example, organoids according to the present disclosure can have a diameter between 200 μm and 300 μm. In another example, organoids according to the present disclosure can have a diameter between 250 μm and 300 μm.

It will be appreciated by the person skilled in the art that organoid size can be measured by, for example, light microscopy and accompanying software such as ImageJ. For example, one of skill in the art can identify organoids of an above exemplified size by measuring the width across the widest point of their three dimensional structure.

In another example, organoids according to the present disclosure remain viable in culture for at least three weeks. In another example, organoids according to the present disclosure remain viable in culture for at least four weeks. In another example, organoids according to the present disclosure remain viable in culture for at least six weeks. In another example, organoids according to the present disclosure remain viable in culture for at least three to four weeks. For example, kidney organoids disclosed herein may only develop diffusion limitations (i.e. limitations affecting transfer of nutrients to cells comprising the organoid structure) after three to six weeks in culture. In these examples the referenced period of time is measured from D7+1. Accordingly, put another way organoids according to the present disclosure remain viable in culture until at least D7+21, D7+28 or D7+42. In an example, cell proliferation rates can be used as a measure of diffusion limitation. This is because cells will not typically continue to divide in the absence of sufficient nutrients. Accordingly, cell proliferation in organoids disclosed herein can be tracked over time to determine when diffusion limitations occur. In an example, a reduction in cell proliferation rate over a 3 to 6 day period indicates diffusion limitations. In another example, a plateau in cell proliferation over a 3 to 6 day period indicates diffusion limitations.

The present disclosure encompasses a kidney organoid comprising a small number of nephrons compared to the human kidney. Those of skill in the art will appreciate that kidney organoids are artificial products and, while they share a number of physiological and biochemical hallmarks of mammalian kidneys, they do not occur naturally. For example, kidney organoids disclosed herein may not be connected to intact vasculature, and/or one or more of the following features:
- have less than 50 nephrons;
- include about $0.5 \times 10^4$ to $8 \times 10^4$ cells;
- have a diameter of less than 1000 μm (preferably about 250 to 350 μm);
- are independent 3-dimensional structures that are not part of a tissue or an organ; and,
- are produced by a method involving differentiation of stem cells in vitro.

Cellular Compositions and Method of Treatment

Organoids or cells of the present disclosure can be used to produce therapeutic compositions. In an example, whole organoids disclosed herein can be provided as a therapeutic composition. In another example, the present disclosure encompasses a cellular composition produced from a kidney organoid disclosed herein. In example, a cellular composition is prepared by enzymatically digesting an organoid according to the present disclosure. For example, a cellular composition can be prepared by digesting an organoid defined herein using a protease such as trypsin either alone or in combination with Ethylenediaminetetraacetic acid (EDTA). In another example, a cellular composition can be prepared by digesting an organoid defined herein with a collagenase such as Collagenase I and/or Collagenase II (e.g. commercially available liberasem (Roche)). In an example, the enzymatic digest is partially purified or purified to deplete one or more cell types. For example, vascular and/or endothelial cells can be depleted. In another example, the enzymatic digest is partially purified or purified to enrich one or more cell types. For example, the enzymatic digest can be partially purified or purified to provide an enriched composition of nephron progenitors and/or ureteric epithelial progenitor cells.

In another example, compositions encompassed by the present disclosure comprise cells cultured using a method disclosed herein. For example, compositions can comprise improved IM cells expressing high levels of PAX2, LHX1 and OSR1 (cap mesenchyme) and Wnt11 and GATA3 (ureteric epithelium). As in the above example, IM cells can be cultured using a method defined herein and partially purified or purified to enrich one or more cell types such as nephron progenitors and/or ureteric epithelial progenitors.

Accordingly, in another example, the present disclosure encompasses a cellular composition comprising a population of nephron progenitor cells and/or ureteric epithelial progenitor cells purified from an organoid or cell population produced by a method defined herein.

In an example, therapeutic compositions disclosed herein comprise a pharmaceutically acceptable carrier and/or excipient. The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980)). A carrier may also reduce any undesirable side effects of the active compound. A suitable carrier is, for example, stable, e.g., incapable of reacting with other ingredients in the composition. In one example, the carrier does not produce significant local or systemic adverse effect in recipients at the dosages and concentrations employed for treatment.

Suitable carriers for the present disclosure include those conventionally used, e.g., saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a medium composition, e.g., in which a cell or whole organoid is grown or suspended. For example, such a medium composition does not induce any adverse effects in a subject to whom it is administered. In an example, the cell culture medium may comprise a basal medium disclosed herein. In an example, the basal medium may comprise PVA and MC. For example, the basal medium may comprise 0.05 to 0.5% PVA and 0.05 to 0.5% MC.

In one example, the carrier or excipient provides a buffering activity to maintain the cells at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a kidney or a region surrounding or adjacent to a kidney, e.g., by injection. Accordingly, in an example, cellular compositions or whole organoids disclosed herein are provided in phosphate buffered saline (PBS).

In another example, cell compositions or whole organoids can be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds. A variety of different scaffolds may be used successfully in the practice of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. J. Ped. Surg. 23:3-9 1988; Cima, et al. Biotechnol. Bioeng. 38:145 1991; Vacanti, et al. Plast. Reconstr. Surg. 88:753-9 1991; or synthetic polymers such as polyanhydrides, polyorthoesters, and polylactic acid. In another example, cells may be administered in a gel scaffold (such as Gelfoam from Upjohn Company). In another example, cells may be administered in a de-cellularised kidney scaffold. In an example, cells may be administered in a de-cellularised human kidney or extracellular matrix (ECM) component thereof.

In an example, the composition comprises an effective amount or a therapeutically effective amount of cells or whole organoids. In another example, cells or whole organoids are contained within a chamber that does not permit the cells or organoids to exit into a subject's circulation, however that permits factors secreted by the cells or organoids to enter the circulation. In this manner soluble factors may be administered to a subject by permitting the cells or organoids to secrete the factors into the subject's circulation. Such a chamber may equally be implanted at a site in a subject to increase local levels of the soluble factors, e.g., implanted in or near the kidney.

In an example, compositions disclosed herein may be administered systemically, such as, for example, by intravenous, intra-arterial, or intraperitoneal administration. In an example, compositions disclosed herein are administered intravenously. In another example, compositions are administered intra-arterially. In another example, compositions are administered via renal artery injection, renal parenchymal injection or subcapsular transplantation into normal or diseased kidneys. In another example, compositions are implanted. For example, whole organoids can be implanted in close proximity to a subject's kidney.

In an example, a cellular composition according to the present disclosure may be cryopreserved. Cryopreservation of cells or whole organoids can be carried out using slow-rate cooling methods or 'fast' freezing protocols known in the art. Preferably, the method of cryopreservation maintains similar phenotypes, cell surface markers and growth rates of cryopreserved cells or whole organoids in comparison with unfrozen cells or whole organoids. The cryopreserved composition may comprise a cryopreservation solution. The pH of the cryopreservation solution is typically 6.5 to 8, preferably 7.4.

Examples, of cyropreservation solutions comprise, non-pyrogenic isotonic solution such as, for example, Plasma-Lyte A®. 100 mL of PlasmaLyte A® contains 526 mg of sodium chloride, USP (NaCl); 502 mg of sodium gluconate ($C_6H_{11}NaO_7$); 368 mg of sodium acetate trihydrate, USP ($C_2H_3NaO_2 \cdot 3H_2O$); 37 mg of potassium chloride, USP (KCl); and 30 mg of magnesium chloride, USP ($MgCl_2 \cdot 6H_2O$). It contains no antimicrobial agents.

In an example, the present disclosure encompasses a method of cellular therapy, the method comprising administering a composition disclosed herein to a subject in need thereof. For example, the present disclosure encompasses a method of treating kidney disease by administering a composition disclosed herein to a subject in need thereof. The term "kidney disease" is used in the context of the present disclosure to refer to disorders associated with any stage or degree of acute or chronic renal failure that results in a loss of the kidney's ability to perform the function of blood filtration and elimination of excess fluid, electrolytes, and wastes from the blood. Examples of kidney disease include endocrine dysfunctions such as anemia (erythropoietin-deficiency), and mineral imbalance (Vitamin D deficiency). Kidney disease may also originate in the kidney or may be secondary to a variety of conditions, including (but not limited to) heart failure, hypertension, diabetes, autoimmune disease, or liver disease or drug induced toxicity. In an example, kidney disease may be a condition of chronic renal failure that develops after an acute injury to the kidney. For example, injury to the kidney by ischemia and/or exposure to toxicants may cause acute renal failure; incomplete recovery after acute kidney injury may lead to the development of chronic renal failure. Other examples of kidney disease include congenital nephrotic syndrome (CNS) including steroid resistant nephrotic syndrome and Finnish nephropathy, focal segmental glomerulonephritis (FSGS), Alport syndrome and Pierson syndrome.

In an example, the present disclosure encompasses a method of treating kidney disease by implanting a whole organoid disclosed herein into a subject in need thereof. In another example, the present disclosure encompasses a method of treating kidney disease by administering a cellular composition disclosed herein to a subject in need thereof.

In other examples, compositions or cells disclosed herein can be provided for the re-cellularisation of a de-cellularised kidney scaffold. In another example, the present disclosure encompasses a biomaterial or scaffold comprising composition or cells disclosed herein.

Stem Cells

Aspects of the present disclosure encompass culture of stem cells. The term "stem cell" is used in the context of the present disclosure to refers to a subset of progenitors that have the capacity or potential, under particular circumstances, to differentiate to a more specialized or differentiated phenotype, and which retain the capacity, under certain circumstances, to proliferate without substantially differentiating. In one example, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only.

In an example, the stem cells are human stem cells. In an example, the stem cells are a population of culture expanded human stem cells. In an example, stem cells can be culture expanded in-vitro or ex-vivo. In an example, culture expanded stem cells have been passaged at least once, twice, three, four, five, six, seven, eight, nine, 10 times.

In an example, the stem cells are pluripotent stem cells. In another example, stem cells are human embryonic stem cells. Generally, pluripotent stem cells show expression of OCT4, NANOG and SSEA1 when in a pluripotent state and expression of these markers is generally lost with differentiation. In another example, stem cells are human embryonic stem cells. The terms "human embryonic stem cell" and abbreviations thereof such as "hES" and "hESC" refer to cells derived, obtainable or originating from human embryos or blastocysts, which are self-renewing and pluri- or toti-potent, having the ability to yield all of the cell types present in a mature animal. Human embryonic stem cells (hESCs) can be isolated, for example, from human blastocysts obtained from human in vivo preimplantation embryos, in vitro fertilized embryos, or one-cell human embryos expanded to the blastocyst stage.

In another example, the stem cells are induced pluripotent stem cells. For example, the stem cells can be human induced pluripotent stem cells. The term "induced pluripotent stem cell" and abbreviation thereof "iPSC" refer to cells derivable, obtainable or originating from human adult somatic cells of any type reprogrammed to a pluripotent state through the expression of exogenous genes, such as transcription factors, including a preferred combination of OCT4, SOX2, KLF4 and c-MYC. Human iPSC show levels of pluripotency equivalent to hESC but can be derived from a patient for autologous therapy with or without concurrent gene correction prior to differentiation and cell delivery. Suitable processes for generation of induced pluripotent stem cells are described, for example, in U.S. Pat. No. 7,615,374 and US 2014273211, Barberi et al; Plos medicine, Vol 2(6):0554-0559 (2005), and Vodyanik et al. Cell Stem cell, Vol 7:718-728 (2010). In an example, iPSC are derived from fibroblasts. In another example, iPSC are derived from blood. For example, iPSC can be derived from white blood cells. In another example, iPSC are derived from fibroblasts. In another example, iPSC are derived from white blood cells or fibroblasts.

In an example, the stem cells are H9 or hES3. Accordingly, in an example, the present disclosure encompasses a kidney organoid disclosed herein, wherein the kidney organoid is derived from H9 stem cells. In another example, the present disclosure encompasses a kidney organoid disclosed herein, wherein the kidney organoid is derived from hES3 stem cells (Kao et al., 2016; Ng et al., 2016; van den Berg et al., 2018). For example, the kidney organoids can be derived from hES3-SOX17mCherry or H9 GAPTrapLuc2. Accordingly, in an example, the present disclosure encompasses a kidney organoid comprising less than 50 nephrons, wherein the kidney organoid is derived from H9 or hES3 stem cells. In another example, the kidney organoid comprises less than 15 nephrons and is derived from H9 or hES3 stem cells. In these examples, the stem cells can express a reporter gene.

In another example, the stem cells are iPSC GAPTrap td-Tomato, CRL1502.C32 or CLR1502.3 (Briggs et al., 2013; Takasato et al., 2015). Accordingly, in an example, the present disclosure encompasses kidney organoids defined herein, wherein the kidney organoids are derived from iPSC GAPTrap td-Tomato. Accordingly, in an example, the present disclosure encompasses a kidney organoid comprising less than 50 nephrons, wherein the kidney organoid is derived from iPSC GAPTrap td-Tomato, CRL1502.C32 or CLR1502.3. In another example, the kidney organoid comprises less than 15 nephrons and is derived from iPSC GAPTrap td-Tomato, CRL1502.C32 or CLR1502.3. Again, in these example, the stem cells can express a reporter gene.

In an example, it may be desirable to produce kidney organoid that is representative of a particular subject and/or disease. Various examples of this embodiment are described below. Relevant to this section is the iPS cells that may be used to produce the kidney organoid. In an example, the human iPS cells are derived from a human subject with a genetic kidney disease. In this example, a blood sample may be isolated from the subject with a genetic kidney disease and iPS cells may be induced from cells in the blood sample (e.g. white blood cells). The subject may have one of various exemplary genetic kidney diseases. Examples include congenital nephrotic syndrome (CNS) including steroid resistant nephrotic syndrome and Finnish nephropathy, focal segmental glomerulonephritis (FSGS), Alport syndrome and Pierson syndrome. Accordingly, in an example, the present disclosure encompasses kidney organoids that are representative of a kidney disease selected from the group consisting of congenital nephrotic syndrome (CNS) including steroid resistant nephrotic syndrome and Finnish nephropathy, focal segmental glomerulonephritis (FSGS), Alport syndrome and Pierson syndrome. Accordingly, in an example, the kidney organoids are representative of CNS. In another example, the kidney organoids are representative of steroid resistant nephrotic syndrome.

In an example, kidney organoids can be used to model the developing kidney and/or kidney disease. Accordingly, in an example, the present disclosure encompasses a kidney organoid disclosed herein, wherein the kidney organoid is used for modelling kidney development. In another example, the present disclosure encompasses a kidney organoid disclosed herein, wherein the kidney organoid is used for modelling kidney disease. In an example, the kidney disease is CNS or another of the above referenced diseases. In this example, disease can be modelled by inducing iPS cells from subjects with an above referenced kidney disease and producing kidney organoids therefrom. In this example, gene editing can be employed (e.g. CRISPR/Cas9 gene editing) to introduce mutations into genes of the subject derived iPS cells that are relevant or potentially relevant to kidney disease development. In other examples, gene editing is employed to correct mutations in the subject derived iPS cells. In an example, isogenic gene edited iPS cells can be generated (e.g. Forbes et al. (2018) Am J Hum Genet. 102:816-831). Kidney development and disease can be modelled over time (e.g. 2, 5, 10 or more days) using kidney organoids at various developmental stages such as one or more of those discussed below (e.g. d7+15). In these examples, organoid glomeruli may be cultured in groups with each group being representative of a different developmental stage (e.g. d7+11, d7+15, d7+18, d7+20) and/or being cultured for a defined period of time (e.g. 2, 5, and 10 days in swirler culture). Kidney organoids can be assessed using for example, visual assessment, immunohistochemistry, gene and protein expression analysis to determine developmental or disease stage. In an example, kidney organoids can also be contacted with a nephrotoxin, candidate compound and/or therapeutic compound during these studies and nephrotoxicity and/or therapeutic efficacy can be determined. As noted above, kidney organoids used in the above examples can be generated from iPS cells that have been genetically modified to express a reporter gene.

Cell Culture Methods

The term "media" or "medium" as used in reference to cell culture, includes the components of the environment surrounding the cells. It is envisaged that the medium contributes to and/or provides the conditions sufficient for cell differentiation and organoid formation. Medium may be solid, liquid, gaseous or a mixture of phases and materials. Medium can include liquid growth medium as well as liquid medium that do not sustain cell growth. Medium also include gelatinous medium such as agar, agarose, gelatin and collagen matrices. Exemplary gaseous medium include the gaseous phase that cells growing on a petri dish or other solid or semisolid support are exposed to. The term "medium" also refers to material that is intended for use in a cell culture, even if it has not yet been contacted with cells.

The culture medium used in the method of the present disclosure can be prepared by using a culture medium used for culturing of stem cells or IM cells as a basal culture medium. The basal culture medium includes, for example, Eagles minimal essential (MEM) culture medium and is not particularly restricted providing it can be used for culturing of stem cells or IM cells. Further, the culture medium of the present disclosure can contain any components such as fatty acids or lipids, vitamins, growth factors, cytokines, antioxidants, buffering agents, inorganic salts and the like. The cell culture medium used in the present disclosure contains all essential amino acids and may also contain non-essential amino acids. In general, amino acids are classified into essential amino acids (Thr, Met, Val, Leu, Ile, Phe, Trp, Lys, His) and non-essential amino acids (Gly, Ala, Ser, Cys, Gln, Asn, Asp, Tyr, Arg, Pro). In other examples, the basal culture medium includes for example APEL™, mTESR™-E6 or E8™ chemically defined medium (StemCell Technologies). Basal culture media may also be supplemented with protein free hybridoma media (PFHM) (e.g. 3.5%). In an example, basal media is supplemented with a serum replacement. For example, basal culture media can be supplemented with knockout serum replacement (Thermo Fisher).

As will be appreciated by those of skill in the art, culture medium disclosed herein will need to be replaced over time. Identifying the appropriate timing for media replacement is considered to be well within the skill set of said skilled addressee. For example, there are various commercially available colorimetric indicators commonly used in cell culture media to indicate when media requires replacement. As a guide, for cell culture in multi-well culture dishes, culture media can be replaced every 24 or 48 hours. For example, culture media can be replaced every two days.

Kidney Organoids

The present disclosure encompasses a method of producing kidney organoids. In an example, kidney organoids are produced by swirling culture medium comprising a population of intermediate mesoderm (IM) cells. In an example, the IM cells are swirled in suspension culture. For the avoidance of doubt, "suspension culture" is used in the context of the present disclosure to refer to cell culture in which single cells or small aggregates of cells multiply while suspended in agitated liquid medium. For example, the single cells or small aggregates of cells multiply in suspension culture and form kidney organoids.

In an example, the IM cell culture medium comprises FGF. In some examples, the FGF may be selected from the FGF9 super family, which includes FGF9, FGF16 and FGF20. In some examples, the FGF is FGF9. For example, the IM cell culture medium can comprises FGF from D7 to at least D7+10. In an example, the IM cell culture medium can comprises FGF from D7 to at least D7+15. Example concentrations of FGF are provided below. For example, the cell culture medium comprises at least 50 ng/ml FGF. In another example, the cell culture medium comprises at least 100 ng/ml FGF. In another example, the cell culture medium comprises at least 150 ng/ml FGF. In another example, the cell culture medium comprises at least 200 ng/ml FGF. In another example, the cell culture medium comprises at least 300 ng/ml FGF. In another example, the cell culture medium comprises at least 350 ng/ml FGF. In another example, the cell culture medium comprises at least 400 ng/ml FGF. In another example, the cell culture medium comprises at least 500 ng/ml FGF. In another example, the cell culture medium comprises between 50 ng/ml and 400 ng/ml FGF. In another example, the cell culture medium comprises between 50 ng/ml and 300 ng/ml FGF. In another example, the cell culture medium comprises between 50 ng/ml and 250 ng/ml FGF. In another example, the cell culture medium comprises between 100 ng/ml and 200 ng/ml FGF. In another example, the cell culture medium comprises between 180 ng/ml and 220 ng/ml FGF. In another example, the cell culture medium comprises between 190 ng/ml and 210 ng/ml FGF.

In an example, the IM cell culture medium can comprise FGF9. In an example, the cell culture medium comprises at least 50 ng/ml FGF9. In another example, the cell culture medium comprises at least 100 ng/ml FGF9. In another example, the cell culture medium comprises at least 150 ng/ml FGF9. In another example, the cell culture medium comprises at least 200 ng/ml FGF9. In another example, the cell culture medium comprises at least 300 ng/ml FGF9. In another example, the cell culture medium comprises at least 350 ng/ml FGF9. In another example, the cell culture medium comprises at least 400 ng/ml FGF9. In another example, the cell culture medium comprises at least 500 ng/ml FGF9. In another example, the cell culture medium comprises between 50 ng/ml and 400 ng/ml FGF9. In another example, the cell culture medium comprises between 50 ng/ml and 300 ng/ml FGF9. In another example, the cell culture medium comprises between 50 ng/ml and 250 ng/ml FGF9. In another example, the cell culture medium comprises between 100 ng/ml and 200 ng/ml FGF9. In another example, the cell culture medium comprises between 180 ng/ml and 220 ng/ml FGF9. In another example, the cell culture medium comprises between 190 ng/ml and 210 ng/ml FGF9.

In another example, an above referenced level of FGF9 is substituted for FGF2. For example, the IM cell culture medium can comprise between 50 ng/ml and 400 ng/ml FGF2. In another example, the cell culture medium comprises between 50 ng/ml and 300 ng/ml FGF2. In another example, the cell culture medium comprises between 50 ng/ml and 250 ng/ml FGF2. In another example, the cell culture medium comprises between 100 ng/ml and 200 ng/ml FGF2. In another example, the cell culture medium comprises between 180 ng/ml and 220 ng/ml FGF2. In another example, the cell culture medium comprises between 190 ng/ml and 210 ng/ml FGF2.

In another example, an above referenced level of FGF9 is substituted for FGF16. For example, the IM cell culture medium can comprise between 50 ng/ml and 400 ng/ml FGF16. In another example, the cell culture medium comprises between 50 ng/ml and 300 ng/ml FGF16. In another example, the cell culture medium comprises between 50 ng/ml and 250 ng/ml FGF16. In another example, the cell culture medium comprises between 100 ng/ml and 200 ng/ml FGF16. In another example, the cell culture medium comprises between 180 ng/ml and 220 ng/ml FGF16. In another example, the cell culture medium comprises between 190 ng/ml and 210 ng/ml FGF16.

In another example, an above referenced level of FGF9 is substituted for FGF20. For example, the IM cell culture medium can comprise between 50 ng/ml and 400 ng/ml FGF20. In another example, the cell culture medium comprises between 50 ng/ml and 300 ng/ml FGF20. In another example, the cell culture medium comprises between 50 ng/ml and 250 ng/ml FGF20. In another example, the cell culture medium comprises between 100 ng/ml and 200 ng/ml FGF20. In another example, the cell culture medium comprises between 180 ng/ml and 220 ng/ml FGF20. In another example, the cell culture medium comprises between 190 ng/ml and 210 ng/ml FGF20. In an example, FGF is removed from the culture media after 5 days in swirler culture. In an example, FGF is removed from the culture media after 6 days in swirler culture. In an example, FGF is removed from the culture media following 4 to 6 days of swirler culture.

In an example, nephrogenesis is initiated in organoids by supplementing the culture medium with a Wnt/β-catenin agonist. The term "Wnt/β-catenin agonist" is used in the context of the present disclosure to refer to a molecule that inhibits GSK3 (e.g GSK3-β) in the context of the canonical Wnt signalling pathway, but preferably not in the context of other non-canonical, Wnt signalling pathways. In some examples, the Wnt/β-catenin agonist is a GSK 3β inhibitor. Examples of Wnt β-catenin agonists include CHIR99021 (CHIR), LiCl, SB-216763, CAS 853220-52-7 and other Wnt/β-catenin agonists that are commercially available from sources such as Santa Cruz Biotechnology and R & D Systems.

Accordingly, in an example, the IM cell culture medium can comprise an above referenced level of FGF and a Wnt/β-catenin agonist. For example, the IM cell culture medium can comprise at least 0.5 µM of Wnt/β-catenin agonist. In another example, the cell culture medium can comprise at least 0.6 µM of Wnt/β-catenin agonist. In another example, the cell culture medium can comprise at least 0.7 µM of Wnt/β-catenin agonist. In another example, the cell culture medium can comprise at least 0.8 µM of Wnt/β-catenin agonist. In another example, the cell culture medium can comprise at least 0.9 µM of Wnt/β-catenin agonist. In another example, the cell culture medium can comprise about 1 µM of Wnt/β-catenin agonist. In another example, the cell culture medium can comprise 1.1 µM or less of Wnt/β-catenin agonist. In another example, the cell culture medium can comprise 1.2 µM or less of Wnt/β-catenin agonist. In another example, the cell culture medium can comprise 1.3 µM or less of Wnt/β-catenin agonist. In another example, the cell culture medium can comprise 1.4 µM or less of Wnt/β-catenin agonist. In another example, the cell culture medium can comprise 1.5 µM or less of Wnt/β-catenin agonist. It will be appreciated that the culture medium can comprise any combination of these upper and lower limits on the concentration of the Wnt/β-catenin agonist. In another example, the cell culture medium can comprise between 0.5 µM and 1.5 µM of Wnt/β-catenin agonist. In another example, the cell culture medium can comprise between 0.8 µM and 1.2 µM of Wnt/β-catenin agonist. In an example, the cell culture medium can comprise at least 0.5 µM CHIR. In another example, the cell culture medium can comprise at least 0.6 µM CHIR. In another example, the cell culture medium can comprise at least 0.7 µM CHIR. In another example, the cell culture medium can comprise at least 0.8 µM CHIR. In another example, the cell culture medium can comprise at least 0.9 µM CHIR. In another example, the cell culture medium can comprise about 1 µM CHIR. In another example, the cell culture medium can comprise 1.1 µM or less CHIR. In another example, the cell culture medium can comprise 1.2 µM or less CHIR. In another example, the cell culture medium can comprise 1.3 µM or less CHIR. In another example, the cell culture medium can comprise 1.4 µM or less CHIR. In another example, the cell culture medium can comprise 1.5 µM or less CHIR. It will be appreciated that the culture medium can comprise any combination of these upper and lower limits on the concentration of CHIR. In another example, the cell culture medium can comprise between 0.5 µM and 1.5 µM CHIR. In another example, the cell culture medium can comprise between 0.8 µM and 1.2 µM CHIR.

In another example, the IM cell culture medium can comprise a Rho kinase inhibitor (ROCKi) such as Y-27632 (StemCell Technologies). In an example, the cell culture medium can comprise at least 8 µM ROCKi. In another example, the cell culture medium can comprise about 10 µM ROCKi. In another example, the cell culture medium can comprise 12 µM or less ROCKi. In another example, the cell culture medium can comprise between 8 µM and 12 µM ROCKi.

In an above example, the IM cell culture medium can comprise FGF9, a Wnt/β-catenin agonist such as CHIR and one or more or all of Heparin, poly(vinyl alcohol) (PVA) and methyl cellulose (MC). In another example, the cell culture medium can also comprise ROCKi.

In an example, the IM cell culture medium comprises at least 0.5 µg/ml heparin. In another example, the cell culture medium comprises about 1 µg/ml heparin. In another example, the cell culture medium comprises 1.5 µg/ml or less heparin. In another example, the cell culture medium comprises 2 µg/ml or less heparin. In another example, the cell culture medium comprises between 0.2 µg/ml and 2 µg/ml heparin. In another example, the cell culture medium comprises between 0.5 µg/ml and 1.5 µg/ml heparin. In another example, the cell culture medium comprises between 0.8 µg/ml and 1.2 µg/ml heparin.

In an example, the IM cell culture medium comprises at least 0.05% PVA. In another example, the cell culture medium comprises about 0.1% PVA. In another example, the cell culture medium comprises 0.15% or less PVA. In another example, the cell culture medium comprises between 0.1% and 0.15% PVA.

In an example, the IM cell culture medium comprises at least 0.05% MC. In another example, the cell culture medium comprises about 0.1% MC. In another example, the cell culture medium comprises less than 0.15% MC. In another example, the cell culture medium comprises between 0.1% and 0.15% MC.

The terms "swirled", "swirl" and "swirling" are used interchangeably in the context of the present disclosure to refer to the movement of cell culture medium in a circular, twisting or spiralling pattern. In one example, cell culture medium is swirled by applying sufficient agitation in a circular motion to a cell culture. For example, cell cultures can be swirled using an orbital shaker. Other examples of apparatus suitable for swirling cell cultures include shaker platforms, shaker incubators or spinning flasks. Appropriate rpm for swirling allows IM cells to aggregate and form organoids.

In an example, the IM cell culture is swirled at least at 30 rpm. In another example, the cell culture is swirled at least at 40 rpm. In another example, the cell culture is swirled at least at 50 rpm. In another example, the cell culture is swirled at least at 60 rpm. In another example, the cell culture is swirled at least at 70 rpm. In another example, the cell culture is swirled at least at 80 rpm. In another example, the cell culture is swirled at between 40 and 80 rpm. In another example, the cell culture is swirled at between 50 and 70 rpm. In another example, the cell culture is swirled at between 55 and 65 rpm. In another example, the cell culture is swirled at between 30 and 150 rpm. In another example, the cell culture is swirled at between 30 and 90 rpm.

In an example, IM cells are cultured for at least five days. In another example, IM cells are cultured for at least seven days. In another example, IM cells are cultured for at least ten days. In another example, IM cells are cultured for at least 12 days. In another example, IM cells are cultured for at least 14 days. In another example, IM cells are cultured for at least 20 days. In another example, IM cells are cultured for up to 42 days. In another example, IM cells are cultured for between 5 and 20 days. In another example, IM cells are cultured for between five and 18 days. In another example, IM cells are cultured for between seven and 14 days. For example, IM cells can be culture with swirling for at least ten days. For example, IM cells can be swirled for at least 20 days. In another example, IM cells can be swirled for at least 30 days. In an example, IM cells are swirled for between 10 and 30 days. In another example, IM cells are swirled for between 15 and 30 days.

In an example, a population of IM cells is dissociated and cultured with swirling in above referenced culture media. In an example, IM cells can be dissociated using EDTA. In another example, IM cells can be dissociated using trypsin or TrypLE™. In an example, dissociated IM cells are passed through a mesh screen before being cultured further. In an example, cells are cultured with swirling for at least 12 days after dissociation. In another example, cells are cultured with swirling for at least 13 days after dissociation. In another example, cells are cultured with swirling for at least 14 days after dissociation. In another example, cells are cultured with swirling for at least 15 days after dissociation. In another example, cells are cultured with swirling for at least 20 days after dissociation. In another example, cells are cultured with swirling for at least 25 days after dissociation. In another example, cells are cultured with swirling for at least 35 days after dissociation. In another example, cells are cultured with swirling for 5 to 18 days after dissociation.

In other examples, IM cells defined herein can be cultured in various culture mediums comprising different components. For example, cells can be cultured in stages wherein each stage is associated with a different culture medium. In an example, IM cells are cultured with swirling in two stages. In this example, stage 1 culture medium comprises an above referenced level of FGF such as FGF9, CHIR, ROCKi, heparin, PVA and MC while stage 2 culture medium comprises an above referenced level of FGF such as FGF9, CHIR, heparin, PVA and MC. For example, stage 1 culture medium can comprise 200 ng/ml FGF9, 1 µM CHIR, 10 µM ROCKi, 1 µg/ml heparin, 0.1% PVA and 0.1% MC while stage 2 culture medium can comprise FGF9, 1 µM CHIR, 1 µg/ml heparin, 0.1% PVA and 0.1% MC.

In another example, IM cells are cultured with swirling in three stages. In this example, stage 1 and 2 culture mediums are as defined above and stage 3 culture medium comprises an above referenced level of PVA and MC. For example, stage 3 culture medium can comprise 0.1% PVA and 0.1% MC.

In an example, IM cells are cultured in stage 1 culture medium for one day before being cultured in stage two culture medium for four days. In an example, cells are cultured in stage 1 culture medium for 18 to 24 hours before being cultured in stage 2 culture medium for four days. In these examples, cells may be further cultured in stage three culture medium for seven to 20 days. In another example, cells may be further cultured in stage three culture medium for at least 15 days. In another example, cells may be further cultured in stage three culture medium for at least 30 days.

The present inventors have also identified that the addition of a retinoic acid to IM cells after about 5 to 10 days in swirler culture improves glomerular maturation in organoids (improved glomerular podocyte maturation). Accordingly, in an example, retinoic acid is added to the cell culture medium after 5 to 10 days in swirler culture. In an example, all trans retinoic acid (atRA) is added to cell culture medium. In an example, at least 0.07 µM retinoic acid is added to the cell culture medium. In another example, at least 0.1 µM retinoic acid is added to the cell culture medium. In another example, at least 0.2 µM retinoic acid is added to the cell culture medium. In another example, at least 0.5 µM retinoic acid is added to the cell culture medium.

In another example, at least 1.5 µM retinoic acid is added to the cell culture medium. In an example, at least 1.8 µM retinoic acid is added to the cell culture medium. In an example, at least 2.0 μM retinoic acid is added to the cell culture medium. In another example, at least 2.5 μM retinoic acid is added to the cell culture medium. In another example, between 1.5 μM and 3 μM retinoic acid is added to the cell culture medium. In another example, between 2.0 μM and 3 μM retinoic acid is added to the cell culture medium.

In another example, stage 1 and 2 culture mediums are as defined above and stage 3 culture medium comprises an above referenced level of PVA, MC and atRA. For example, stage 3 culture medium can comprise 0.1% PVA and 0.1% MC. 2.5 μM atRA.

The present inventors have identified that subjecting a low number of IM cells to swirler culture in appropriate medium can direct development of kidney organoids having a simplified three dimensional structure. Accordingly, in an example, the methods of the present disclosure encompass swirling a population of IM cells which comprises less than $5\times10^5$ IM cells. In another example, the methods of the present disclosure encompass swirling a population of IM cells which comprises less than $4\times10^5$ IM cells. In another example, the methods of the present disclosure encompass swirling a population of IM cells which comprises less than $3\times10^5$ IM cells. In another example, the methods of the present disclosure encompass swirling a population of IM cells which comprises less than $1\times10^5$ IM cells. In another example, the methods of the present disclosure encompass swirling a population of IM cells which comprises $5\times10^4$ IM cells. In another example, the methods of the present disclosure encompass swirling a population of IM cells which comprises $4\times10^4$ IM cells. In another example, the methods of the present disclosure encompass swirling a population of IM cells which comprises between $1\times10^4$ and $1\times10^5$ IM cells. In another example, the methods of the present disclosure encompass swirling a population of IM cells which comprises between $2\times10^4$ and $1\times10^5$ IM cells. In another example, the methods of the present disclosure encompass swirling a population of IM cells which comprises between $5\times10^3$ and $3\times10^5$ IM cells.

In another example, the methods of the present disclosure encompass swirling between $1\times10^5$ IM cells/ml to $5\times10^6$ IM cells/ml. In another example, the methods of the present disclosure encompass swirling between $5\times10^5$ and $4\times10^6$ IM cells/ml. In another example, the methods of the present disclosure encompass swirling between $5\times10^5$ and $3\times10^6$ IM cells/ml. In other examples, the methods of the present disclosure encompass swirling a population of less than $5\times10^6$ IM cells/ml. In another example, the methods of the present disclosure encompass swirling a population of less than $4\times10^6$ IM cells/ml. In another example, the methods of the present disclosure encompass swirling a population of less than $3\times10^6$ IM cells/ml. In another example, the methods of the present disclosure encompass swirling a population of less than $2\times10^6$ IM cells/ml. In another example, the methods of the present disclosure encompass swirling a population of $1\times10^6$ IM cells/ml or lower. In another example, the methods of the present disclosure encompass swirling between $5\times10^5$ and $2\times10^6$ IM cells/ml. In another example, the methods of the present disclosure encompass swirling between $5\times10^5$ and $1.5\times10^6$ IM cells/ml. In these examples, around 5,000 to 15,000 organoids may be produced. In another example, around 8,000 to 10,000 organoids may be produced. In these examples, the total cell number increases from the cell number at the start of swirler culture by 30 to 40 fold over the duration of culturing. In these examples, the total cell number increases by 3 to 4 fold compared to the increase in total cell number using the protocol described in Takasato et al. (2015) Nature, Vol. 526:564-568. In this example, the total cell number increases from about $1\times10^5$ to $5\times10^6$ cells/ml to about $3\times10^6$ to $2\times10^8$ cells/ml.

In an example, the IM cells are obtained via a method disclosed herein.

In an example, the present disclosure encompasses a method of producing kidney organoids which comprises:
  culturing a population of stem cells for seven days to produce IM cells, wherein the first 4 to 5 days involve culturing the stem cells in high concentration of a Wnt/β-catenin agonist such as CHIR and the remaining days involve culturing the cells in a cell culture medium comprising FGF9 and a low concentration of a Wnt/β-catenin agonist;
  dissociating the IM cells;
  producing kidney organoids by swirling IM cells in a cell culture medium comprising FGF9 for at least 5 days, wherein the first 24 hours involves culturing the cells in cell culture medium comprising FGF9, heparin, a low concentration of Wnt/β-catenin agonist and ROCKi and the following 3 or 4 days involves culturing the cells in cell culture medium comprising FGF9, heparin, a low concentration of Wnt/β-catenin agonist PVA and MC.

In the above example, stem cells can be cultured for seven days, wherein the first 4 days involve culturing the stem cells in high concentration of a Wnt/β-catenin agonist such as CHIR and the remaining days involve culturing the cells in a cell culture medium comprising FGF9 and a low concentration of a Wnt/β-catenin agonist. In an example, the Wnt/β-catenin agonist is CHIR. In an example, a high concentration of CHIR is from about 3 μM to about 12 μM. In another example, a high concentration of CHIR is from about 4 μM to about 10 μM, from about 5 μM to about 9 μM, about 6 μM to about 8 μM, about 6.5 μM to about 8 μM, or about 6.5 μM to about 7 μM. In an example, a low concentration of CHIR is 1 μM. In an example, IM cells are dissociated using trypsin. In another example, cells are dissociated using EDTA. In an example, IM cells are swirled in a cell culture medium comprising 200 ng/ml FGF9 for at least 4 days, wherein the first 24 hours involves culturing the cells in cell culture medium comprising 200 ng/ml FGF9, 1 μg/ml heparin, 1 μM CHIR and 10 μM ROCKi and the following 3 or 4 days involves culturing the cells in cell culture medium comprising 200 ng/ml FGF9, 1 μg/ml heparin, 1 μM, 0.1% PVA and 0.1% MC.

In another example, the method further comprises swirling the cells in a cell culture medium comprising PVA and MC which does not comprise CHIR or FGF9. In an example, the cell culture medium comprises 0.1% PVA and 0.1% MC. In an example, cells are swirled in cell culture medium comprising PVA and MC which does not comprise CHIR or FGF9 for 5 days or longer.

Intermediate Mesoderm

The present inventors have also surprisingly identified that culturing stem cells in medium comprising a low concentration of CHIR and activating wnt/β-catenin signalling for a longer duration is beneficial in producing improved intermediate mesoderm. The in vitro culture method provides a system for differentiating stem cells through posterior primitive streak (PPS) cells and intermediate mesoderm (IM) cells to produce the kidney organoid.

Accordingly, in an example, the present disclosure encompasses an in-vitro method of producing intermediate mesoderm (IM) cells, the method comprising, culturing a population of posterior primitive streak (PPS) cells for 2 to 5 days in a cell culture medium comprising FGF and less than 4 µM of a Wnt/β-catenin agonist. Suitable concentrations of FGF and Wnt/β-catenin agonists and duration of culturing are as described below in relation to the method of producing intermediate mesoderm (IM) cells for the time period after the first 3 or 4 days of culture.

Accordingly, in an example, the present disclosure encompasses a method of producing intermediate mesoderm (IM) cells, the method comprising, culturing a population of stem cells in a cell culture medium comprising CHIR for around 7 days, wherein a FGF such as FGF9 is added to the culture media after the first 3 or 4 days of culture. In an example, from 50 ng/ml to 400 ng/ml FGF9 is added to the culture media after the first 3 or 4 days of culture. In another example, from 50 ng/ml to 300 ng/ml FGF9 is added to the culture media after the first 3 or 4 days of culture. In another example, from 50 ng/ml to 250 ng/ml FGF9 is added to the culture media after the first 3 or 4 days of culture. In another example, from 100 ng/ml to 200 ng/ml FGF9 is added to the culture media after the first 3 or 4 days of culture. In another example, from 150 ng/ml to 250 ng/ml FGF9 is added to the culture media after the first 3 or 4 days of culture. In another example, from 175 ng/ml to 225 ng/ml FGF9 is added to the culture media after the first 3 or 4 days of culture. In another example, from 190 ng/ml to 210 ng/ml FGF9 is added to the culture media after the first 3 or 4 days of culture. In another example, from 195 ng/ml to 205 ng/ml FGF9 is added to the culture media after the first 3 or 4 days of culture. In another example, about 200 ng/ml FGF9 is added to the culture media after the first 3 or 4 days of culture. In an example, heparin is also added to the culture media after the first 3 or 4 days of culture. In an example, between 0.5 µg/ml and 2 µg/ml heparin is added to the culture media after the first 3 or 4 days of culture. In another example, between 0.5 µg/ml and 1.5 µg/ml heparin is added to the culture media after the first 3 or 4 days of culture. In another example, between 0.8 µg/ml and 1.2 µg/ml heparin is added to the culture media after the first 3 or 4 days of culture. In another example, 1 µg/ml heparin is added to the culture media after the first 3 or 4 days of culture. In an example, an above referenced level of FGF and heparin is added to the culture media after 4 days in culture. In an example, the stem cells are cultured in a cell culture medium comprising CHIR for 7 days.

In particular, the present inventors have identified that culturing stem cells in a high concentration of Wnt/β-catenin agonist such as CHIR followed by culturing the stem cells in a low concentration of Wnt/β-catenin agonist and a FGF such as FGF9 produces improved IM cells. For example, the improved IM cells express high levels of PAX2, LHX1 and OSR1 (cap mesenchyme) and Wnt11 and GATA3 (ureteric epithelium). Accordingly, in an example, stem cells can be cultured in culture medium comprising a high concentration of Wnt/β-catenin agonist such as CHIR before being cultured in a culture medium comprising a low concentration of Wnt/β-catenin agonist and a FGF such as FGF9, FGF16, FGF20 or FGF2.

In an example, the present disclosure encompasses a method of producing intermediate mesoderm (IM) cells, the method comprising, culturing a population of stem cells in a cell culture medium comprising a high concentration of CHIR before culturing the population of stem cells in a cell culture medium comprising a low concentration of CHIR and a FGF such as FGF9. In this example, a "high concentration" of CHIR is at least 5 µM and a "low concentration" of CHIR is less than 3 µM. In another example, a "high concentration" of CHIR is at least 6 µM and a "low concentration" of CHIR is less than 2 µM. In another example, a "high concentration" of CHIR is 7 µM and a "low concentration" of CHIR is 1 µM or less.

Accordingly, in another aspect, the methods of the present disclosure encompass an in-vitro method of producing intermediate mesoderm (IM) cells. In an example, the method of producing IM cells comprises, culturing a population of stem cells for around seven days, wherein the first 4 to 5 days involve culturing the stem cells in high concentration of a Wnt/β-catenin agonist such as CHIR and the remaining days involve culturing the cells in a cell culture medium comprising FGF9 and a low concentration of a Wnt/β-catenin agonist. In one aspect, the method of producing IM cells comprises, culturing a population of stem cells in a cell culture medium comprising FGF9 and at least 0.5 µM of a Wnt/β-catenin agonist after the first 4 to 5 days of culture in high concentration of a Wnt/β-catenin agonist. In another example, the cell culture medium can comprise at least 0.6 µM of Wnt/β-catenin agonist after the first 4 to 5 days of culture in high concentration of a Wnt/β-catenin agonist. In another example, the cell culture medium can comprise at least 0.7 µM of Wnt/β-catenin agonist after the first 4 to 5 days of culture in high concentration of a Wnt/β-catenin agonist. In another example, the cell culture medium can comprise at least 0.8 µM of Wnt/β-catenin agonist after the first 4 to 5 days of culture in high concentration of a Wnt/β-catenin agonist. In another example, the cell culture medium can comprise at least 0.9 µM of Wnt/β-catenin agonist after the first 4 to 5 days of culture in high concentration of a Wnt/β-catenin agonist. In another example, the cell culture medium can comprise about 1 µM of Wnt/β-catenin agonist after the first 4 to 5 days of culture in high concentration of a Wnt/β-catenin agonist. In another example, the cell culture medium can comprise 1.1 µM or less of Wnt/β-catenin agonist after the first 4 to 5 days of culture in high concentration of a Wnt/β-catenin agonist. In another example, the cell culture medium can comprise 1.2 µM or less of Wnt/β-catenin agonist after the first 4 to 5 days of culture in high concentration of a Wnt/β-catenin agonist. In another example, the cell culture medium can comprise 1.3 µM or less of Wnt/β-catenin agonist after the first 4 to 5 days of culture in high concentration of a Wnt/β-catenin agonist. In another example, the cell culture medium can comprise 1.4 µM or less of Wnt/β-catenin agonist after the first 4 to 5 days of culture in high concentration of a Wnt/β-catenin agonist. In another example, the cell culture medium can comprise 1.5 µM or less of Wnt/β-catenin agonist after the first 4 to 5 days of culture in high concentration of a Wnt/β-catenin agonist. It will be appreciated that the culture medium can comprise any combination of these upper and lower limits on the concentration of the Wnt/β-catenin agonist after the first 4 to 5 days of culture in high concentration of a Wnt/β-catenin agonist. In another example, the cell culture medium can comprise between 0.5 µM and 1.5 µM of Wnt/β-catenin agonist after the first 4 to 5 days of culture in high concentration of a Wnt/β-catenin agonist. In another example, the cell culture medium can comprise between 0.8 µM and 1.2 µM of Wnt/s-catenin agonist after the first 4 to 5 days of culture in high concentration of a Wnt/β-catenin agonist. Accordingly, in an example, the cell culture medium can comprise less than 2 µM of Wnt/β-catenin agonist after the first 4 to 5 days of culture in high concentration of a Wnt/β-catenin agonist. In another example, the cell culture medium can comprise less than 1.5 µM of Wnt/β-catenin agonist after the first 4 to 5 days of culture in high concentration of a Wnt/β-catenin agonist.

In an example, the Wnt/β-catenin agonist is CHIR. Accordingly, in an example, the cell culture medium can comprise at least 0.5 µM CHIR after the first 4 to 5 days of culture in high concentration of CHIR. In another example, the cell culture medium can comprise at least 0.6 µM CHIR after the first 4 to 5 days of culture in high concentration of CHIR. In another example, the cell culture medium can comprise at least 0.7 µM CHIR after the first 4 to 5 days of culture in high concentration of CHIR. In another example, the cell culture medium can comprise at least 0.8 µM CHIR after the first 4 to 5 days of culture in high concentration of CHIR. In another example, the cell culture medium can comprise at least 0.9 µM CHIR after the first 4 to 5 days of culture in high concentration of CHIR. In another example, the cell culture medium can comprise about 1 µM CHIR after the first 4 to 5 days of culture in high concentration of CHIR. In another example, the cell culture medium can comprise between 0.5 µM and 1.5 µM CHIR after the first 4 to 5 days of culture in high concentration of CHIR. In another example, the cell culture medium can comprise between 0.8 µM and 1.2 µM CHIR after the first 4 to 5 days of culture in high concentration of CHIR. Accordingly, in an example, the cell culture medium can comprise less than 2 µM CHIR after the first 4 to 5 days of culture in high concentration of CHIR. In another example, the cell culture medium can comprise less than 1.5 µM CHIR after the first 4 to 5 days of culture in high concentration of CHIR.

In an example, the culture medium can comprise a low concentration of CHIR such as those exemplified above and FGF9 after the first 4 to 5 days of culture in high concentration of CHIR. In an example, the cell culture medium comprises at least 50 ng/ml FGF9. In another example, the cell culture medium comprises at least 100 ng/ml FGF9. In another example, the cell culture medium comprises at least 150 ng/ml FGF9. In another example, the cell culture medium comprises at least 200 ng/ml FGF9. In another example, the cell culture medium comprises at least 300 ng/ml FGF9. In another example, the cell culture medium comprises at least 350 ng/ml FGF9. In another example, the cell culture medium comprises at least 400 ng/ml FGF9. In another example, the cell culture medium comprises at least 500 ng/ml FGF9. In another example, the cell culture medium comprises between 50 ng/ml and 400 ng/ml FGF9. In another example, the cell culture medium comprises between 50 ng/ml and 300 ng/ml FGF9. In another example, the cell culture medium comprises between 50 ng/ml and 250 ng/ml FGF9. In another example, the cell culture medium comprises between 100 ng/ml and 200 ng/ml FGF9. In another example, the cell culture medium comprises between 180 ng/ml and 220 ng/ml FGF9. In another example, the cell culture medium comprises between 190 ng/ml and 210 ng/ml FGF9.

In another example, an above referenced level of FGF9 is substituted for FGF2. For example, the cell culture medium can comprise between 50 ng/ml and 400 ng/ml FGF2. In another example, the cell culture medium comprises between 50 ng/ml and 300 ng/ml FGF2. In another example, the cell culture medium comprises between 50 ng/ml and 250 ng/ml FGF2. In another example, the cell culture medium comprises between 100 ng/ml and 200 ng/ml FGF2. In another example, the cell culture medium comprises between 180 ng/ml and 220 ng/ml FGF2. In another example, the cell culture medium comprises between 190 ng/ml and 210 ng/ml FGF2.

In another example, an above referenced level of FGF9 is substituted for FGF16. For example, the cell culture medium can comprise between 50 ng/ml and 400 ng/ml FGF16. In another example, the cell culture medium comprises between 50 ng/ml and 300 ng/ml FGF16. In another example, the cell culture medium comprises between 50 ng/ml and 250 ng/ml FGF16. In another example, the cell culture medium comprises between 100 ng/ml and 200 ng/ml FGF16. In another example, the cell culture medium comprises between 180 ng/ml and 220 ng/ml FGF16. In another example, the cell culture medium comprises between 190 ng/ml and 210 ng/ml FGF16.

In another example, an above referenced level of FGF9 is substituted for FGF20. For example, the cell culture medium can comprise between 50 ng/ml and 400 ng/ml FGF20. In another example, the cell culture medium comprises between 50 ng/ml and 300 ng/ml FGF20. In another example, the cell culture medium comprises between 50 ng/ml and 250 ng/ml FGF20. In another example, the cell culture medium comprises between 100 ng/ml and 200 ng/ml FGF20. In another example, the cell culture medium comprises between 180 ng/ml and 220 ng/ml FGF20. In another example, the cell culture medium comprises between 190 ng/ml and 210 ng/ml FGF20.

In an example, the culture medium comprising high concentration CHIR does not comprise FGF.

In another example, the cell culture medium can comprise a low concentration of CHIR such as those exemplified above, an above exemplified level of FGF and heparin after the first 4 to 5 days of culture in high concentration of CHIR. In an example, the cell culture medium comprising low concentration of CHIR and FGF also comprises heparin. In this example, the cell culture medium can comprise 1 µg/ml heparin. In another example, the cell culture medium can comprise 1.5 µg/ml heparin. In another example, the cell culture medium can comprise 2 µg/ml heparin. In another example, the cell culture medium can comprise between 0.5 µg/ml and 2 µg/ml heparin. In another example, the cell culture medium can comprise between 0.5 µg/ml and 1.5 µg/ml heparin. In another example, the cell culture medium can comprise between 0.8 µg/ml and 1.2 µg/ml heparin.

In an example, the methods of the present disclosure encompass combining an above referenced method of producing IM cells and using these IM cells in an above exemplified method of producing a kidney organoid.

In an example, stem cells can be cultured using an above referenced method to produce IM cells before being dissociated and cultured in an above referenced swirler culture to produce kidney organoids. In this example, IM cells can be dissociated using EDTA, trypsin or TrypLE™. In another example, cells can be dissociated using EDTA before being passed through a mesh screen and cultured in an above referenced swirler culture to produce kidney organoids. In another example, cells can be dissociated using trypsin before being centrifuged and resuspending the resulting pellet in an above referenced swirler culture to produce kidney organoids.

Kidney organoids encompassed by the present disclosure can be described based on number of days in culture. The days in culture can be separated into two components including days for production of IM cells from stem cells (X) and days for formation of kidney organoid from IM cells (Y). In an example, the step distinguishing production of IM cells from stem cells and production of kidney organoid from IM cells is the dissociation of IM cells. One way of representing the days in culture for production of IM cells from stem cells and days for formation of kidney organoid from IM cells is day (d) X+Y (e.g. d7+12 would describe 7 days of producing IM cells from stem cells followed by dissociation of IM cells and 12 days of organoid formation from IM cells (i.e. Y=number of days as an organoid).

In an example, kidney organoids encompassed by the present disclosure are a d7+12 kidney organoids. In another example, kidney organoids encompassed by the present disclosure are d7+14 kidney organoid. In another example, kidney organoids encompassed by the present disclosure are d7+15 or later kidney organoids. In another example, kidney organoids encompassed by the present disclosure are d7+17 kidney organoids.

In another example, kidney organoids encompassed by the present disclosure are d7+20 kidney organoids. In another example, kidney organoids encompassed by the present disclosure are d7+22 kidney organoid. In another example, kidney organoids encompassed by the present disclosure are d7+25 kidney organoid. In another example, kidney organoids encompassed by the present disclosure are d7+30 kidney organoid. In another example, kidney organoids encompassed by the present disclosure are between d7+13 and d7+30. In another example, kidney organoids encompassed by the present disclosure are between d7+14 and d7+30. In another example, kidney organoids encompassed by the present disclosure are between d7+15 and d7+30. In another example, kidney organoids encompassed by the present disclosure are between d7+15 and d7+25. In the above referenced examples IM cells may be cultured for 8, 9 or 10 days (i.e. d8+Y, d9+Y or d10+Y).

In another example, cells of kidney organoids disclosed herein proliferate after D7+7. In another example, cells of kidney organoids disclosed herein proliferate after D7+10. In another example, cells of kidney organoids disclosed herein proliferate after D7+12. In another example, cells of kidney organoids disclosed herein proliferate between D7+5 and D7+10. In another example, cells of kidney organoids disclosed herein proliferate between D7+5 and D7+12. In these examples, cell proliferation can be detected by preparing a population of organoids using methods disclosed herein and, isolating and dissociating organoids from the population at specific time points (e.g. D7+5, D7+7, D7+10 etc.) and determining cell numbers at each time point using for example, a trypan blue dye exclusion test in an automated cell counter (e.g. Life Technologies).

Screening

Kidney organoids encompassed by the present disclosure can be used in various screening applications. In an example, kidney organoids can be used to screen for toxicity. For example, kidney organoids can be used to screen for nephrotoxicity.

Accordingly, in an example, the present disclosure encompasses a method of screening a candidate compound for nephrotoxicity, the method comprising contacting a kidney organoid disclosed herein with a candidate compound and determining whether or not the candidate compound is nephrotoxic.

In an example a kidney organoid described herein is contacted with a candidate compound before being assessed for nephrotoxic side effects. Exemplary nephrotoxic side effects include direct tubular effects, podocyte injury, interstitial nephritis and glomerulonephritis. Nephrotoxicity can also be assessed or measured by any appropriate test for kidney cell function in vitro, including analysis of biomarker expression using commercially available tools including, for example, the Human Nephrotoxicity RT$^2$ Profiler™ PCR Array from Qiagen or the High Content Analysis (HCA) Multiplexed Nephrotoxicity Assay from Eurofins. In another example, nephrotoxicity is assessed by measuring acute apoptosis of glomerular cells in kidney organoids disclosed herein following contact with a candidate compound. In other examples, nephrotoxicity can be assessed using electron microscopy such as transmission EM or scanning EM. Other examples of criteria indicative of nephrotoxicity include loss of podocyte marker gene expression or protein expression and loss of foot processes (loss of effacement).

In another example, the present disclosure encompasses a method of screening a candidate compound for therapeutic efficacy in treating kidney disease, the method comprising contacting kidney organoids disclosed herein with a candidate compound under conditions to determine whether or not the candidate compound is therapeutically effective. In this example, the method may comprise contacting kidney organoids disclosed herein with a candidate compound in the presence of a nephrotoxic compound and determining whether or not the candidate compound is therapeutically effective.

Other examples of screening for therapeutic efficacy include assessing kidney organoids that are representative of a kidney disease. For example, the kidney disease can be selected from the group consisting of congenital nephrotic syndrome (CNS) including steroid resistant nephrotic syndrome and Finnish nephropathy, focal segmental glomerulonephritis (FSGS), Alport syndrome and Pierson syndrome. In an example, the kidney disease is CNS.

The term "therapeutic efficacy" is used in the context of the present disclosure to refer to a response in which any toxic or detrimental effects of a candidate compound or composition comprising the same is outweighed by the therapeutically beneficial effects. Therapeutic efficacy can be determined based on improved kidney cell function; maintained kidney cell function; inhibition (i.e., slowing to some extent and, in some examples, stopping) decline in kidney cell function; inhibiting (i.e., slowing to some extent and, in some examples, stopping) kidney cell death. In an example, therapeutic efficacy is determined based on the presence of appropriate podocyte proteins and evidence that they are appropriately polarised. An example includes localisation of NPHS1, NPHS2 and NEPH-1 at the membrane of podocytes, wherein NPHS1, NPHS2 and NEPH-1 is determined using immunohistochemistry.

For studies involving kidney organoids that are representative of a kidney disease, nephrotoxicity and therapeutic efficacy can be determined relative to a pre-determined standard ascertained based on corresponding kidney cell function in a disease-free kidney organoid. In another example, improved kidney cell function may be determined based on a comparison of kidney cell function between a kidney organoid representative of kidney disease and a kidney organoid representative of healthy kidney.

For studies involving contacting kidney organoids with a nephrotoxic compound and a candidate compound, improved kidney cell function may be determined based on a comparison with kidney organoids that are not contacted with the nephrotoxic compound and/or kidney organoids contacted with nephrotoxic compound alone.

The term "candidate compound" is used in the context of the present disclosure to refer to an agent to be screened. Candidate compounds may include, for example, small molecules such as small organic compounds (e.g., organic molecules having a molecular weight between about 50 and about 2,500 Da), peptides or mimetics thereof, ligands including peptide and non-peptide ligands, polypeptides, nucleic acid molecules such as aptamers, peptide nucleic acid molecules, and components, combinations, and derivatives thereof.

It is considered that terms such as "contacting", "exposing" or "applying" are terms that can, in context, be used interchangeably in the present disclosure. The term contacting, requires that the candidate compound(s) be brought into contact with a glomerulus disclosed herein. In an example, the compound can be dissolved in cell culture media if the compound is water soluble or water-immiscible. Otherwise, a suitable substrate may be soaked in the compound and placed over kidney organoids in culture. For the screening of volatile candidate compounds, kidney organoids disclosed herein can be exposed to air or other gas mixtures comprising the compound(s). Alternatively, kidney organoids can be exposed to a solution or suspension of the volatile compound in cell culture media. Again, if possible, volatile compounds can be dissolved or stabilised. Otherwise, a suitable substrate may be soaked in the compound and placed over kidney organoids in culture.

In performing the methods of the present disclosure a plurality of candidate compounds can be contacted with kidney organoids. For example, at least 2, at least 3, at least 4, at least 5, at least 6, at least 7, at least 8, at least 9, at least 10, least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 70, at least 80, at least 90, at least 100, at least 200, at least 300, at least 400, at least 500, at least 600, at least 700, at least 800, at least 900, at least 1,000, at least 2,000, at least 3,000, at least 5,000, at least 10,000, at least 20,000, at least 40,000, at least 50,000, at least 100,000, at least 200,000 or more candidate compounds can be contacted with kidney organoids. In an example, candidate compounds can be contacted with the same or separate kidney organoids. For example, specific combinations of candidate compounds can be screened.

In an example, candidate compounds are labelled prior to screening. In an example, the candidate compound can be a composition. For example, the candidate compound may be present in a formulation or comprise a mixture of compounds or molecules. For example, the candidate compound can be serum. For example, the candidate compound can be serum isolated from a subject with kidney disease. In an example, the serum is isolated from a subject with CNS. For example, the serum can be isolated from a subject that has steroid resistant nephrotic syndrome. In another example, the serum is isolated from a subject that has had a kidney transplant. In another example, the serum is isolated from a subject with nephrotic syndrome that has presented post-kidney transplant.

Exemplary nephrotoxins include aminoglycoside antibiotics, β lactam antibiotics, cisplatin, radiocontrast media, NSAIDs, ACE inhibitors, lithium, CsA and anti-epileptic drugs such as phenytoin.

Kidney organoids cultured for various lengths of time can be used in screening applications disclosed herein. Thus, as one example, d7+15 or later kidney organoids can be used in screening. In another example, between d7+18 and d7+25 kidney organoids can be used in screening. In another example, immature kidney organoids can be used in screening. For example, between d7+11 and d7+18 can be used in screening. In various examples, IM cells may be cultured for longer and thus d8+Y, d9+Y or d10+Y kidney organoids can be used in screening.

In an example, the screening method comprises contacting candidate compound(s) with a library of kidney organoids. For example, candidate compounds can be screened using kidney organoids at different developmental stages. For example, d7+10, d7+15 and d7+25 kidney organoids can be used. In another example, candidate compounds can be screened using kidney organoids representative of different kidney diseases.

As the skilled person would appreciate, there are a wide variety of different screening procedures which could be adapted to screen candidate compounds. For example, kidney organoids disclosed herein can be provided in a single or multiwell format and contacted with candidate compounds for a set period of time. In an example, kidney organoids are provided in a multi-well plate. In an example, one kidney organoid is provided per well. In another example, two kidney organoids are provided per well. In another example, three kidney organoids are provided per well. In another example, four kidney organoids are provided per well. In another example, five kidney organoids are provided per well. In another example, 10 kidney organoids are provided per well. In another example, 20 or more kidney organoids are provided per well. In an example, the kidney organoids are provided in a 96 well plate.

High throughput screening methods are encompassed by the present disclosure. In this example, high throughput screening involves providing a library containing a large number of candidate compounds. Such libraries are then screened in one or more assays to identify those library members (e.g. particular chemical species or subclasses) that display a desired level of activity (e.g. therapeutic efficacy).

High throughput screening systems are commercially available and typically automate entire procedures, including all sample and reagent pipetting, liquid dispensing, timed incubations, and final readings of a culture plate (e.g. 96 well formats) in detectors appropriate for the assay. These configurable systems provide rapid start up as well as a high degree of flexibility and customization. The manufacturers of such systems (e.g. Invitrogen, Thermo Fisher Scientific etc.) provide detailed protocols for use.

In an example, the above referenced methods further comprise selecting a compound which displays therapeutic efficacy. For example, compounds that, in the presence of a nephrotoxin and/or when contacted with kidney organoids representative of kidney disease, maintain kidney cell function; inhibit (i.e., slow to some extent and, in some examples, stop) decline in kidney cell function; inhibit (i.e., slow to some extent and, in some examples, stop) kidney cell death. In another example, the above referenced methods further comprise selecting a compound which reduces nephrotoxicity. For example, compounds that inhibit glomerulonephritis can be selected. In another example, compounds that improve kidney cell function may be selected. In these examples, kidney cell function may be determined based on biomarker expression using commercially available tools including, for example, the Human Nephrotoxicity RT$^2$ Profiler™ PCR Array from Qiagen or the High Content.

Personalised Medicine and Stratification

A candidate compound showing therapeutic efficacy in kidney organoids representative of kidney disease in a subject may be more likely to display therapeutic efficacy in the subject. Accordingly, in an example, these kidney organoids can be used to select agents that are more likely to affect treatment or prophylaxis of kidney disease in the subject.

In another example, kidney organoids representative of a kidney disease in multiple subjects can be prepared. These kidney organoids can be used to select agents that are more likely to affect treatment or prophylaxis of kidney disease in multiple subjects or identify groups of subjects that are more likely to respond to treatment with a particular agent. Such methods may be useful for stratifying subjects in clinical trials of agents being tested for capacity to treat kidney disease. Grouping subject populations based on kidney organoid screening may eliminate or reduce variation in treatment outcome due to genetic factors, leading to a more accurate assessment of the efficacy of a potential drug. Accordingly, in an example, the present disclosure encompasses a method for stratifying a group of subjects for a clinical trial of a therapeutic agent, the method comprising obtaining an iPS cell population from a group of subjects generating a kidney organoid or population thereof from each subjects iPS cell population, contacting the kidney organoids with a therapeutic agent, determining whether the therapeutic agent is therapeutically effective and using the results of the determination to select subjects more likely to be responsive to the therapy. In this example, the method may comprise contacting kidney organoids with a therapeutic agent and a nephrotoxin before determining whether the therapeutic agent is therapeutically effective. Examples of therapeutic agents include candidate compounds discussed above such as, for example, one or more small molecules, polynucleotides, peptides, proteins, antibodies, antibody fragments, viruses, bacteria, stem cells, serum including kidney disease patient derived serum. For the avoidance of doubt, serum can be isolated from a subject with a particular kidney disease and contacted with kidney organoids disclosed herein. Various examples of kidney disease are discussed herein and serum can be isolated from various subjects representative of these diseases. Methods of isolating serum from subjects are known in the art. In an example, serum is purified from a whole blood sample using centrifugation.

Bio-Printing

In an example, the present disclosure encompasses "bio-printed" kidney structures such as kidneys or other nephron-containing organs, organoids or organ-like structures produced using compositions or cells disclosed herein. Terms such as "bioprinted" or "bioprinting" are used in the context of the present disclosure to refer to a process utilizing three-dimensional, precise deposition of cells (e.g., cell solutions, cell-containing gels, cell suspensions, cell concentrations, multicellular aggregates, multicellular bodies, bio-ink etc.) via methodology that is compatible with an automated, computer-aided, three-dimensional prototyping device (e.g. a bio-printer). Examples of methods suitable for bio-printing are disclosed in WO 2012/054195 and WO 2013/040087. In an example, bio-printing is performed using an organ printing machine which uses a hydrogel scaffold to place human cells in a desired orientation to recreate human organs (e.g. Organovo/Invetech).

In an example, kidney structures are bio-printed from bio-ink. The term "bio-ink" is used in the context of the present disclosure to refer to a liquid, semi-solid, or solid composition comprising compositions or cells defined herein. In an example, bio-ink comprises cell solutions, cell aggregates, cell-comprising gels, multicellular bodies, or tissues. In another example, the bio-ink additionally comprises support material.

Bio-printed kidney structures encompassed by the present disclosure have one or more functional characteristics of a kidney or component thereof, or are capable of developing one or more functional characteristics of a kidney or component thereof. For example, a bio-printed kidney structure may comprise glomerulus, juxtaglomerular apparatus, interstitial tissue, collecting duct, Bowman's capsule, proximal and/or distal convoluted tubules. In an example, the bio-printed kidney structure is not vascularised. In another example, the bio-printed kidney structure comprises vasculature such as arterioles, arteries, veins and/or capillaries.

In an example, the bioprinted kidney structure is implantable or otherwise adoptively transferrable into a host.

Compositions/Kits

In one example, the present disclosure relates to a kit or assay for use in screening applications. For example, the present disclosure encompasses a kit or assay for use in screening candidate compounds for nephrotoxicity and/or therapeutic efficacy. In an example, kidney organoids described herein are provided in culture, candidate compounds can then be contacted with kidney organoids and screened for nephrotoxicity and/or therapeutic efficacy. Accordingly, in an example, the present disclosure encompasses an assay when used for screening, the assay comprising kidney organoids disclosed herein in culture. In an example, the assay is used for nephrotoxicity screening. In an example, the assay is used for therapeutic efficacy screening. In an example, kidney organoids are provided with culture media or other components for maintaining kidney organoids in culture. In an example, kidney organoids are provided with written instructions for performing the methods of the present disclosure. In an example, the assay comprises a kidney organoid described herein. In other examples, the assay comprises more than one kidney organoid. For example, the assay can comprise 10, 20, 30 or more kidney organoids. Kidney organoids can be provided in a single or multi-well format such as a 96 well plate.

EXAMPLES

Example 1—Culturing and Maintenance of hPSC

Human ES cells (H9 cells) were grown on mouse embryonic fibroblast (MEF) feeders in a DMEM media supplemented with 10% KOSR (Life technologies) and bFGF. Cells were cultured to 80% confluency before splitting using TrypLE™ (Life technologies). Before differentiation, ES cells were adapted to Matrigel® (Corning) surface in the absence of MEF feeders in a MEF conditional media and bFGF.

Human iPS cells were grown as individual colonies on Geltrex® (Life technologies) coated plates in an E8™ media (Life technologies). Passaging of the iPS cells was performed once with EDTA once the cells reached 60-70% confluency or every 3 days.

Dissociation of hPSC into single cells was achieved using TrypLE™ and cells were seeded on a Matrigel® coated plated at 15,000 cells/cm². Cell numbers were determined using a haemocytometer. Matrigel® adapted hES cells were seeded using MEF conditional media. Human iPS cells were seeded as single cells in E8™ media using revita cell (1:100 dilution) on Matrigel® coated plate overnight.

Example 2—Production of Improved IM hPSCs or hES were differentiated into intermediate mesoderm by exposing cells to high concentration of CHIR (7 µM) for the first 4 days in APEL™ 2 or TeSR™-E6 media (Stem cell technologies) media with 3.5% protein free hybridoma media (PFHM) (Thermo Fischer), APEL™ (Stem cell technologies) or E6 media (Stem cell technologies). Media was refreshed on day 2. The cultures were subjected to an additional 3 days (days 5 to 7 from seeding) of a low concentration of CHIR (1 µM) in addition to FGF9 and heparin (FIG. 1A, Examples 1-3). This results in induction of a mixture of intermediate mesoderm (IM) cells.

Gene expression profiles performed by qPCR on the swirling suspension cultures at D7+0 showed that addition of a low concentration and longer duration exposure of CHIR resulted in an increase in cap mesenchyme cells compared to shorter exposure (FIG. 1E left panel). The expression of PAX2, LHX1 and OSR1 cells were more than 2 folds higher compared to short CHIR exposure groups (FIG. 1E left panel). Exposure of cells to low concentration of CHIR also resulted in an increase in ureteric epithelium exemplified by greater than 2 fold increase in expression of Wnt11 and GATA3 compared to short CHIR exposure groups (FIG. 1E right panel). The addition of a low concentration of CHIR to activate Wnt/β-catenin signalling for longer duration demonstrates a method of producing improved intermediate mesoderm.

Example 3—Swirling Suspension Cultures

On day 7, IM cells produced using methods in Example 2 were dissociated using 1 ml of EDTA solution, further incubation in 1 ml EDTA for 3 minutes at 37° C. and EDTA solution was removed by aspiration without disturbing the IM cell layer (FIG. 1A). IM cells may also be dissociated using 1.5 ml of TrypLE™ select for 3 minutes at 37° C. and excess TrypLE™ was removed by centrifugation at 1500 RPM in a 15 ml falcon tube. Stage 1 Media (Base media, FGF9 200 ng/ml, Heparin 1 μg/ml, 1 μM CHIR, 0.1% PVA, 0.1% MC) (2 ml) was added along with 10 μM Rho kinase inhibitor (ROCKi, 1:1000 dilution 10 μM, stem cell technologies) and cells were gently detached as a clumps using Gilson pipette. The cell suspension was transferred to 6 cm$^2$ low adhesion dishes (Greiner bio) and passed through 40 μm cell strainers (BD biosciences).

The Stage 1 Media was toped up to 5 ml and the dishes were swirled in a Ratek orbital shaker at 60 rpm in a standard cell culture incubator at 37° C. and 5% $CO_2$. Organoids of 20 to 40 μm diameter spontaneously formed after placing the culture dishes on an orbital shaker within 24 hours. Stage 1 Media was replaced with Stage 2 Media (base media, FGF9 200 ng/ml, Heparin 1 μg/ml, 1 μM CHIR, 0.1% PVA, 0.1% MC) after 24 hours in swirler culture. The cells were cultured in Stage 2 Media for another 4 days. From day 7+5 onwards, all the organoids were refreshed with Stage 3 Media (base media, 0.1% PVA, 0.1% MC) every alternative days and cultured until day 7+18.

After 18 days post-aggregation (Day 7+18), each kidney organoid showed tubular epithelial structures as confirmed by bright-field, periodic acid Schiff (PAS) staining and confocal microscopic analysis confirmed the presence of 6-10 nephrons (FIG. 1 and FIG. 2). These nephrons showed evidence of early patterning and segmentation. The formation of glomeruli was evident from positive staining for NPHS1 and MAFB. Proximal nephron segments were EpCAM$^+$ and stained positive for LTL, CUBN, LRP2 and HNF4A (FIG. 1G). LTL$^+$ segments were able to endocytose FITC-albumin within 24 hours of addition to the culture medium, indicating a functional albumin uptake pathway. Distal nephron segments stained with ECAD and EpCAM while presumptive collecting duct was ECAD$^+$/GATA3$^+$. The presence of endothelial cells (PECAM1$^+$/SOX17$^+$) was also noted when kidney organoids were generated using a SOX17mCherry reporter cell line (Ng et al., 2016) (FIG. 1D; FIGS. 2C, D and E). As an indication of the transferability of the protocol between human pluripotent stem cell lines, data on the successful generation of kidney organoids from 4 different cell lines is provided, including hESC reporter lines (H9 GAPTrapLuc2, hES3-SOX17mCherry) (Kao et al., 2016; Ng et al., 2016; van den Berg et al., 2018) and human iPSCs (CRL1502.C32, CRL1502.3) (Briggs et al., 2013; Takasato et al., 2015). All hPSC lines uniformly responded to the protocol and patterned similarly to kidney organoids (FIG. 2B).

Example 4—Effect of Duration, Concentration and Timing of Canonical Wnt Signalling on Kidney Organoid Patterning To optimise differentiation within the kidney organoid protocol, monolayers of hPSC were stimulated using a fixed concentration of CHIR99021 (7 μM) for varying durations (3, 4, 5 and 6 days) before continued culture to Day 7 in the presence of low CHIR and FGF9+heparin (FIGS. 2C, 2D and 2E). After 18 days, resulting kidney organoids were evaluated for kidney structure using confocal microscopy (FIGS. 2C, 2D and 2E). Canonical Wnt activation for only 3 days failed to generate a kidney morphology (FIG. 2B, left panel). Instead, the epithelial structures present exhibited an undefined epithelium with a large cystic lumen and no evidence of nephron formation. Initial induction with 4 or 5 days of 7 μM CHIR99021 generated kidney organoids containing patterning nephrons, including the presence of surrounding SOX17$^+$ and MEIS1/2/3$^+$ populations suggestive of endothelium and interstitial stromal cells respectively (FIGS. 2C, 2D and 2E, middle panel). However, Wnt activation for 6 days, while generating larger kidney organoids with greater NPHS1 staining, contained an expanded MEIS1$^+$ stromal population apparently compromising epithelial structure (FIGS. 2C, 2D and 2E, right panel). 4 days of initial 7 μM CHIR99021 induction was confirmed as optimal and used in further studies.

Example 5—Dissociation of Kidney Organoids

Kidney organoids represent a heterogeneous epithelial structure of approximately 250-300 μm in diameter. Use of harsh enzymes may destroy cell surface markers leading to the loss of cell identity for later use. Mild dissociation with a cold active protease (Liberase™, Roche) was performed to yield maximum viable single cells. Kidney organoids were transferred to a 15 ml falcon tube using 5 ml serological pipette and allowed to settle. Media supernatant was removed using vacuum, then the organoid pellet was washed three times using 0.1M PBS. The organoids were then treated with 500 μl of 1 μg/ml solution of Liberase™ and incubated at 4° C. for 20 minutes with continued trituration every 5 minutes. After 20 minutes kidney organoids had dissociated into single cells, and were washed twice using DMEM media with 10% FCS to inactivate the Liberasem and the final cell pellet was suspended in DMEM media with 10% FCS.

Example 6—Swirling Intermediate Mesoderm Cells Generates Micro Kidney Organoids in Suspension Culture Existing methods for generating kidney organoids are labour intensive, expensive and produce low quality organoids. The inventors have generated an economical, simple and quick method to generate kidney organoids in suspension culture. In contrast to previous methods, cellular aggregates are formed at the intermediate mesoderm (IM) stage of differentiation (Day 7) as a result of minimal dissociation and low speed swirling of monolayers prior to culture in low adhesion culture plates. This results in the formation of 8,000-10,000 kidney organoids that are much smaller than those produced using previous methods. After 18 days in suspension culture, each kidney organoid comprises around 6-10 nephrons with evidence of early patterning and segmentation, including the formation of proximal and distal epithelium and glomeruli containing podocytes. Importantly, single cell transcriptional profiling has revealed equivalence between these smaller organoids and standard organoids produced using previous methods with respect to cellular diversity and maturity. Using this approach for directed differentiation resulted in a cell expansion of 30-40 fold across 21 days of culture, representing a 3 to 4 fold improvement in yield and a 4 fold reduction in cost per million organoid-derived kidney cells compared to previous approaches such as those based on Takasato et al. (2015) Nature, Vol. 526:564-568.

The disclosed method exemplified in FIG. 1A and described in Examples 1-3 involves addition of 0.1% poly vinyl alcohol (PVA) and 0.1% methyl cellulose (MC) to the culture media of the swirler culture to enhance the cohesive forces of intermediate mesoderm (IM) cells to spontaneously aggregate into 3D spherical organoids. After 24 hours in swirling culture, the organoids formed an outer laminin basement membrane.

C32 organoids cultured for an additional 12 to 18 days were collected, wholemounted and stained for NPHS, LTL, ECAD and GATA3 for confocal microscopic analysis. To evaluate the presence of vasculature the organoids were stained with mouse anti human-CD31 (1:300, BD biosciences), for mature proximal tubule goat anti human-CUBN was used. Immunofluorescence staining analysis of organoids at D7+12 showed the major nephron segmentation in the form of distinct expression of nephrin positive glomeruli, LTL positive proximal tubule, ECAD positive distal tubules and ECAD and GATA3 double positive collecting duct cells including GATA3 positive stromal cells (FIGS. 1G and 4E and F) which was comparable to the transwell organoids system (FIG. 4A). Swirler micro kidney organoids exhibit simple morphology compared to the transwell organoid with respect to the number of nephrons (5 to 10 nephrons in each organoid) and presence of non-kidney cell types.

Together, the results demonstrate a swirling suspension method that generates organoids that are organised and have the capacity to produce complex multicellular kidney organoids with all the nephron segments. The method has been successfully tested with human ES as well as iPS cell lines where organoids were produced. Different basal media conditions such as APEL™, APEL™ 2 and E6™ have been demonstrated to be suitable for the disclosed method. As such, the method is potentially useful for scale up of kidney cell culture for personalised medicine, drug screening and regenerative cell therapy.

Example 7—Micro Kidney Organoids in Suspension Culture Suitable for Scale Up of iPS Derived Kidney Cells To evaluate suspension culture to scale up, C32 iPS cells were differentiated to generate IM as described in Examples 1 and 2. Growth of the organoids was monitored by measuring the size and total number of cells in culture from D7+0 (FIGS. 4C and 4D).

Bright field images of C32 organoid generated using swirler suspension culture showed increase in size and maintained epithelial structures (FIGS. 4A and 4B). Organoid size was measured in bright-field images of up to 10 randomly sampled organoids on NIS-Elements microscopy software (Nikon). Random samples of up to 10 organoids were taken at different growth rate intervals and the diameters of the organoids were measured. Size was reported as low to high range. Consistent increase in the organoid size as time progressed was observed with organoids of 30 μm to 300 μm in diameter detected (FIG. 4C). The total cell number was evaluated after dissociation with TrypLE™ select and manually counted using haemocytometer. A 40 fold increase in cell number by D7+12 to D7+18 compared to seeding density on D7+0 was observed (FIG. 4D).

Example 8—Micro Kidney Organoids in Suspension Culture Show Organised Nephron Segments and Clear Tubular Lumen Classical transwell organoids exhibit complex morphology limiting the ability to study the 3D structure of individual nephrons. Swirler micro kidney organoids produced by the method described herein are much simpler and contain fewer numbers of nephrons.

The organoids exhibit clear 3D morphology allowing for the study of the nephrons in 3D space. C32 derived kidney organoids were generated using the described method of Examples 1-3 and immunostaining was performed using antibodies against NPHS1, LTL, ECAD and GATA3 to visualize the nephron segments in high throughput confocal microscope, Z resolution matching to the pinhole.

Kidney organoids were collected in a 15 ml flacon tube and washed with PBS (two times) to remove excess media and fixed in freshly prepared 2% PFA for 20 minutes at 4° C. Excess PFA was then removed by washing the organoids three time with PBS with 0.3% Triton™X100 (PBST) and stored in PBST at 4° C. until staining. Fixed organoids were blocked in PBST with 10% donkey serum (blocking buffer) for at least 1 hours before incubation with primary antibodies diluted in blocking buffer. Evaluation of the differentiation capacity of kidney organoids was confirmed by staining for major nephron segments, primary antibodies used were: sheep anti human-NPHS1 (1:300 R&D Systems), biotin anti human-LTL (1:300 Vector laboratories), mouse anti human-ECAD (1:300 Life technologies) and rabbit anti human-GATA3 (1:300 Cell signalling technologies) mouse anti human-CD31 (1:300, BD biosciences) and goat anti human-CUBN (1:300 Santa Cruz) and LRP2 (1:300 Sapphire Bioscience). Organoids were incubated in primary antibody for overning at 4° C. then, washed 5 times in PBST, and then incubated with species-matched secondary antibodies with fluorescent labels. After the staining, organoids were dehydrated using different concentrations of methanol followed by clearing using BABB (Benzyl alcohol and Benzyl benzoate, 1:2 ratio) as previously described by Dodt H U et al (Dodt et al., 2007). Cleared organoids were mounted on a MatTek™ glass bottom dish and confocal microscopy was performed using an inverted Zeiss LSM 780 microscope. The images were analysed using the ZEN software (Zeiss).

The images were analysed using Imarism software to reconstruct the 3D rendering of acquired confocal image (FIGS. 4E and 4F). The 3D images showed clear nephron segments connected to each other in a polarized manner starting from glomeruli (NPHS1), proximal tubule (LTL+), distal tubules (ECAD+), collecting duct (ECAD+,GATA3+) and interstitial cells (GATA3+) (FIG. 5E). The use of snipping tools allowed the visualization of the formed lumen in the tubular cells (FIG. 5F). The results of FIGS. 5E and 5F demonstrate that the swirler method described herein is useful in allowing for the study of the morphology of developing kidney organoids in a 3D space.

Example 9—Single Cell RNA Sequencing Analysis Show Promising Kidney Phenotype

To further extensively characterize the swirler kidney organoids, single cell RNA sequencing analysis of C32 derived micro kidney organoids at D7+18 was performed. Approximately 40-50 micro kidney organoids and 1 one entire standard organoid were cultured to day 7+18 using the same hPSC line (CRL1502.C32 in APEL™ media). Organoids were collected and washed 3 times with PBS to remove excess media. Organoids were treated with 400 µl of 1 µg/ml solution of Liberasem (Roche) at 4° C. for 20 minutes by agitation using 1 ml pipette every 5 minutes. Within 20 minutes organoids dissociated into singe cells. Cell culture medial (2 ml) was added to inactive Liberase™. Cells were centrifuged at 1300-1500 rpm for 3-5 minutes to form a pellet. The supernatant was removed, and the pellet was resuspended in fresh DMEM F12 media and passed through 20 µm cell strainers to remove clumps and stored on ice until analysis. Viability and cell number was analysed by FACS and trypan blue dye exclusion test in an automated cell counter (life technologies). Cells were stored on ice until analysis. Cell were thoroughly mixed using wide bore 1 ml pipette tip and approximately 4000 live cells were used for the RNA sequencing analysis. Chromium™ single cell 3' solution developed by 10× genomics technique was used. Sample preparation was done according to the 10× Genomics single cell protocol (Further information available in Chromium™ Single Cell 3' Reagent Kits v2 User Guide accessible online). Single cell suspension, gel beads and partitioning oil will be loaded into the appropriate well of the 10× Chromium™ chip. The chip will be secured with the 10× Gasket and complete assembly will be loaded into the 10× chromium controller. This will automatically generate the suspension of single cell coated in a oil droplets containing unique UMIs for each cell. This suspension will be taken for the conventional RT-PCT to amplify the transcripts.

Cells were barcoded to separately index each cell's transcriptome using a nanoliter-scale Gel Bead-In-EMulsions (GEMs) and UMIs. Magnetic beads are used to remove leftover reagents and primers after barcoding. Full length barcoded cDNA was used to PCR amplify the transcriptome to generate sufficient mass for library construction. These libraries were sequenced simultaneously for UMIs and cDNA fragments in 2 different reads. Library analysis was performed using Cell Ranger™ enabling the study of expression data at single cell resolution. The Cell Ranger pipeline (v1.3.1) was used to perform sample demultiplexing, barcode processing and single-cell gene counting (Zheng et al., 2017). Samples were demultiplexed to produce a pair of FASTQ files for each sample. Reads containing sequence information were aligned to the GRCh38 reference genome. Cell barcodes were filtered to remove empty droplets and PCR duplicates were removed by selecting unique combinations of cell barcodes, UMIs and gene IDs with the final results being a gene expression matrix that was used for further analysis, this enables the study of expression data at single cell resolution. Further analysis was performed to represent cell clustering, cell type classification, and differential gene expression using the Seurat™ R package (version 2.3.1).

Gene expression matrices generated in Cell Ranger were imported into Seurat™ (Satija et al., 2015) for quality control and further analysis. All cells passed initial filtering to remove genes expressed in less than 3 cells, and cells with less than 200 genes expressed. Further filtering removed 1 cell with greater than 15% mitochondrial transcripts. The cyclone function in Sscran (Lun et al., 2016; Scialdone et al., 2015) was used to assign a score related to the likelihood that each cell is in either G1, S or G2M phase, and a cell cycle phase assigned based on this scoring.

Expression data was normalised and scaled, with variability related to the number of UMIs, percentage mitochondrial expression, percentage ribosomal expression and G2M score regressed out using the Seurat™ ScaleData function. Cells were clustered using the shared nearest neighbour modularity optimisation based clustering algorithm implemented in Seurat™ using the first 15 principal components and a resolution value of 1.2. Marker gene lists were generated using the Seurat™ FindAllMarkers function to find differentially expressed genes between clusters, with a log fold change above 0.25.

For combined analysis of standard and kidney organoid datasets gene-cell matrices were generated in Cell Ranger as above. All cells passed initial filtering for genes expressed in less than 3 cells and cells with less than 200 genes. Each dataset was normalised and scaled with regression against the number of UMIs, percentage mitochondrial expression, percentage ribosomal expression and S, G1 and G2M score generated in Scran. Clustering was based on aligned combined components calculated in Seurat™ using the RunCCA and AlignSubspace functions (Butler et al., 2018). For the combined dataset clustering was performed at resolution of 0.6. (Butler et al., 2018).

Single cell RNA gene expression profiling of organoids produced by the method described herein and the classical transwell method were analysed. UMI counts were plotted as tSNE plots and automatic clustering was performed (FIG. 6A-6B) based on the genes present within the cells. The GO enrichment analysis of all the clusters showed 22.3% nephrons, 37.5% total stroma and 9.8% vasculature (FIG. 6A), whereas swirler micro kidney organoids showed 32.5% mature nephron (excluding cap mesenchyme and nephron progenitors), 25.9% stroma, however swirler C32 organoids did not show the presence of vasculature (FIG. 6B). Therefore, the swirler micro kidney organoids showed better markers for kidney development compared to transwell organoids. Micro-kidney organoids also showed enhanced nephron composition compared to transwell cultured organoids (FIG. 4).

Example 10—Transcriptional Validation of Kidney Differentiation within Kidney Organoids Characterisation of the cell types present within kidney organoids was performed using single cell RNA-sequencing (scRNA-seq). A pool of 20-30 kidney organoids was dissociated into viable single cells using cold active protease Liberase™. This resulted in the generation of 89.4% single cells out of which 88.5% cells were live (data not shown). Cell Ranger (10× Genomics) was used to generate a matrix of UMI counts per cell which was imported into for further analysis using the Seurat™ R package (version 2.3.1) (Satija et al., 2015). Filtered data represented 1673 cells with a median of 3759 expressed genes per cell. Clustering using the Seurat™ R package produced 7 distinct cell clusters (FIGS. 3A and 3B, Table 1) at 0.6 resolution. Differential expression testing was performed to identify markers of each cluster and Gene Ontology and functional enrichment analysis for the top significantly up-regulated genes in each cluster was performed using the PANTHER gene ontology suite (Mi et al., 2013; Table 1).

TABLE 1

Gene ontology terms for different clusters with in the kidney micro-organoids.

| Cluster | GO biological process complete | Go Term | Fold Enrichment | FDR |
|---|---|---|---|---|
| 0 | pattern specification involved in pronephros development | GO:0039017 | >100 | 0.01 |
| | pronephric field specification | GO:0039003 | >100 | 0.01 |
| | negative regulation of mesenchymal cell apoptotic process involved in metanephric nephron morphogenesis | GO:0072305 | >100 | 0.01 |
| 1 | metanephric glomerular capillary formation | GO:0072277 | 80.16 | 3.36E−02 |
| | metanephric glomerulus vasculature morphogenesis | GO:0072276 | 80.16 | 3.35E−02 |
| | metanephric glomerulus morphogenesis | GO:0072275 | 80.16 | 3.34E−02 |
| 2 | regulation of cellular response to X-ray | GO:2000683 | >100 | 5.35E−03 |
| | endodermal digestive tract morphogenesis | GO:0061031 | >100 | 7.99E−03 |
| | positive regulation of ureteric bud formation | GO:0072107 | >100 | 1.14E−02 |
| 3 | pattern specification involved in pronephros development | GO:0039017 | 99.73 | 1.80E−02 |
| | pronephric field specification | GO:0039003 | 99.73 | 1.80E−02 |
| | negative regulation of mesenchymal cell apoptotic process involved in metanephric nephron morphogenesis | GO:0072305 | 99.73 | 1.80E−02 |
| 4 | positive regulation of mesenchymal cell apoptotic process | GO:2001055 | 96.97 | 3.43E−02 |
| | negative regulation of neuromuscular junction development | GO:1904397 | 96.97 | 3.41E−02 |
| | corticospinal tract morphogenesis | GO:0021957 | 48.48 | 6.53E−03 |
| 5 | regulation of presynaptic membrane organization | GO:1901629 | >100 | 2.85E−02 |
| | negative regulation of mesenchymal cell apoptotic process involved in nephron morphogenesis | GO:0072040 | 85.31 | 2.71E−03 |
| | regulation of mesenchymal cell apoptotic process involved in nephron morphogenesis | GO:0072039 | 85.31 | 2.69E−03 |
| 6 | neuropilin signaling pathway | GO:0038189 | 32.61 | 1.48E−02 |
| | glomerular capillary formation | GO:0072104 | 26.09 | 2.17E−02 |
| | glomerulus vasculature morphogenesis | GO:0072103 | 26.09 | 2.16E−02 |

While clearly evident using immunofluorescence of whole mount organoid, the endothelium (a subset of Cluster 1) and podocytes (Cluster 6, 18 cells) were represented by only small numbers of individual cells in the scRNA-seq data. Clusters 3 (293 cells) and Cluster 5 (122 cells) showed expression of genes consistent with kidney nephron epithelium with Cluster 0 showing expression of kidney vesicle/ S-shaped body genes (early nephron) while epithelial cell Cluster 5 also showed expression of distal tubule/collecting duct markers such as GFRA1 (FIG. 3C). Cluster 2 showed expression of the nephron progenitor markers SIX1, SIX2 and CITED1, as well as the stromal marker PAX3 that has previously been associated with myogenic Wilms' tumours (Hueber et al., 2009). Cells in Cluster 2 also express markers of myogenic fate such as MYF5 and MYF6, but not PAX7, MYOD1 and TBX6. Cluster 0 (430 cells), which represent the largest clusters, showed a more committed nephron progenitor signature with expression of early kidney vesicle markers PAX2, PAX8, LHX1 and JAG1 as well as the human NP markers LYPD1 and DAPL1 (Lindstrom et al., 2018). Cluster 1 (337 cells) showed a stromal signature like PDGFRB and MEIS2. Cluster 4, while expressing the early nephron marker cadherin CDH6, showed a neural transcriptional signature suggesting the presence of a neural off target population, as has been previously reported in kidney organoids (Wu et al., 2017). This analysis strongly supported the identity of the cell types observed within kidney organoids at the level of immunofluorescence.

Example 11—Comparative Single Cell Transcriptional Profiling of Standard and Kidney Organoids Demonstrates Equivalence of Nephrogenic Patterning In order to directly compare the cellular components within kidney organoids to another kidney organoid method, the kidney organoid scRNA-seq data was combined with data from 1421 kidney organoid cells generated using the same iPSC cell line (CRL1502.C32) and the standard kidney organoid protocol of Takasato et al, 2016. The two datasets were combined using the alignment algorithm implemented in Seurat™ (Butler et al., 2018), which uses correlated component analysis followed by dynamic time warping. Clustering identified 8 transcriptional clusters within the combined dataset, representing committed nephron progenitors (Cluster 0), nephron epithelium (Cluster 6), podocytes (Cluster 7), stroma (Clusters 1 and 3), endothelial cells (cluster 5), PAX3$^{+ve}$ cells (cluster 2) and a neural off-target population (Cluster 4) (FIG. 5A and FIG. 5B). All clusters were represented in both datasets, though the proportion of cells attributed to each cluster varied (FIGS. 5B-5D). A direct comparison of key markers of each cluster shows that, while there were apparent differences in the proportion contributing to each cluster between protocols (FIGS. 5B and 5C), there was strong transcriptional congruence between the cells identified in any given cluster between both protocols (FIG. 5D). The neural off-target population identified in kidney organoids was also evident in standard organoids. Overall, the kidney organoid dataset contained a higher proportion of nephron cells and a lower proportion of stromal cells than standard organoid dataset (FIG. 5E). This increase in PAX2 expressing nephron cells and reduction in MEIS1/2/3 expressing stromal cells in kidney organoids compared to standard organoids was confirmed using immunofluorescence analysis of whole mount organoids (FIG. 5F and FIG. 6).

Example 12—Kidney Organoids Provide a Better Platform for Efficient hPSC Derived Kidney Cell Scale-Up Standard kidney organoids cultured on Transwell™ filters may face diffusion limitations after 3 weeks in culture due to the size of the organoid tissue generated (FIG. 4A). Immunofluorescence staining for the nephron segments after this time suggested a spatial restriction of nephron structures to the edge of the organoids. By way of contrast, kidney organoids contain kidney tubules throughout the structure (FIG. 4B). Kidney organoids can also be formed simultaneously in large numbers using an orbital shaker, avoiding the tedious process of manual handling involved in the standard organoids protocol. As a result, it is possible to generate approximately 8000 to 10000 kidney organoids of uniform size in 5-10 minutes compared to approximately 30 organoids in 60 minutes for standard organoid protocol. Kidney organoids exhibit much smaller final size (250-300 µm) compared to standard organoids (3000-5000 µm) (FIG. 4C). As shown by immunofluorescence, the nephrons forming within a standard organoid are present in a rim around the periphery of the tissue in comparison to the kidney organoids (FIG. 4A). However, these structures are much larger than the kidney organoids. In order to directly compare the efficiency and cost of each approach, standard organoids and kidney organoids, each generated using iPSC and hESC reporter lines, were dissociated to a single cell suspension at multiple time points across the differentiation protocol from Day 7 for quantification of total cell number (FIG. 4D). Standard organoids did not show a substantive change in total cell counts per organoid after Day 7+7, whereas kidney organoids continued to increase in total cell number out to Day 7+12. Overall, cell count increased 8-10 fold under standard organoid conditions but up to 30-40 fold in the case of kidney organoids. This represents a 3 to 4-fold improvement in cell yield using this modified protocol.

Example 13—Addition of all Trans Retinoic Acid Improves Glomerular Podocyte Maturation To determine whether addition of all trans retinoic acid (atRA) would facilitate glomerular maturation of the organoids produced by the swirler culture method described in Examples 1-3, atRA was supplemented in the media after D7+0. All trans retinoic acid (2.5 µM) was added from D7+5 to D7+10 on C32 derived swirler organoids (FIG. 5). After D7+18 immunofluorescence analysis showed that addition of atRA improved the podocyte phenotype compare to the control group (FIGS. 7A and 7B). The results were confirmed by mRNA expression, qPCR analysis of D7+11 and D7+18 samples which showed that addition of 2.5 µM atRA increased expression of glomerular markers such as NPHS1 and proximal tubular markers like CUBN compare to the control (FIG. 7C).

Example 14—Drug Toxicity Testing in Micro Kidney Organoids

To evaluate the suitability of using the suspension culture method described herein to test for drug toxicity of kidneys in vitro, drug toxicity studies were conducted. Organoids produced by the method at day 7+18 were collected and randomized into treatment groups in a 24 well low attachment plates in 250 µl of media. Organoids were stimulated with different concentrations of cytotoxic drug Adriamycin (0, 2.5 and 5 µg/ml) for 24 hours. After stimulation, media was removed and organoids were fixed with 2% PFA for immunofluorescence staining analysis for apoptosis by using TUNEL staining and some organoids were lysed for RNA analysis (FIG. 8A-8D).

Example 15—Summary of Improvments in Kidney Organoid Production

Kidney organoids resulting from the above exemplified methods show reliable formation of kidney nephron epithelial, stromal and endothelial cellular components equivalent at a single cell transcriptional level to those present within previously described kidney organoid protocol (Takasato et al., 2016; Takasato et al., 2015). However, the alterations in culture conditions resulted in a 3-4 fold improvement in relative cell yield at 4 fold less cost per million kidney cells generated. The robustness of the exemplified methods is evidenced by the capacity to recapitulate successful kidney organoid generation using 2 different hESC (H9 and hES3) and 3 different iPSC lines (iPSC GAPTrap td-Tomato, CRL1502.C32 and CLR1502.3), including hES3 SOX17mCherry, H9 GAPTrap Luc2 and iPSC GAPTrap td-Tomato fluorescent reporter lines.

It will be appreciated by persons skilled in the art that numerous variations and/or modifications may be made to the disclosure as shown in the specific embodiments without departing from the spirit or scope of the disclosure as broadly described. The present embodiments are, therefore, to be considered in all respects as illustrative and not restrictive.

The present application claims priority from AU 2017904424 filed 31 Oct. 2017, the disclosures of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Barberi et al., (2005) *Plos Medicine* 2(6): 0554-0559.
Briggs et al., (2013) *Stem Cells* 31: 467-78.

Butler et al., (2018) *Nat Biotechnol* 36: 411-420.
Cima et al., (1991) *Biotechnol. Bioeng.* 38:145 1991.
Dodt et al., (2007) *Nat Methods* 4: 331-6.
Forbes et al., (2018) *Am J Hum Genet.* 102:816-831
Hueber et al., (2009) *Pathol.* 12: 347-54.
Kao et al., (2016) *Stem Cell Reports* 7: 518-526.
Lindstrom et al., (2018) *J Am Soc Nephrol.* 29: 806-824.
Lun et al., (2016) *F1000Res* 5: 2122.
Mi et al., (2013) *Nat Protoc* 8: 1551-1556.
Ng et al., (2016) *Nat Biotechnol* 34: 1168-1179.
Satija et al., (2015) *Nat Biotechnol,* 33: 495-502.
Scialdone et al., (2015) *Methods* 85: 54-61.
Takasato et al., (2015) *Nature* 526: 564-8.
Vacanti, et al., (1988) *J. Ped. Surg.* 23:3-9.
Vacanti, et al., (1991) *Plast. Reconstr. Surg.* 88:753-9.
van den Berg et al., (2018) *Stem Cell Reports* 10: 751-765.
Vodyanik et al., (2010) *Cell Stem cell* 7:718-728.
Wu et al., (2017).
Zheng et al., (2017) *Nat Commun* 8: 14049.

The invention claimed is:

1. An in-vitro method of producing a kidney organoid, the method comprising, swirling a population of dissociated intermediate mesoderm (IM) cells in a cell culture medium comprising fibroblast growth factor (FGF), wherein the kidney organoid comprises NPHS1+ podocytes, LTL+ proximal segments, ECAD+distal segments and ECAD+/GATA3+ collecting ducts, wherein the IM cells are swirled in culture for at least 5 days, wherein the first 24 hours comprise swirling cells in a cell culture medium comprising FGF, heparin, CHIR99021 (CHIR) and rho-associated protein kinase (ROCK) inhibitor.

2. The method of claim 1, wherein after said first 24 hours, the next four days comprise culturing cells in a cell culture medium comprising FGF, heparin and CHIR.

3. The method of claim 1, wherein after the at least 5 days, the culture comprises culturing cells in a cell culture medium comprising poly(vinyl alcohol) (PVA) and methyl cellulose (MC).

4. The method of claim 1, wherein the cell culture media comprise from 100 to 300 ng/ml FGF9.

5. The method according to claim 1, wherein the first 24 hours comprise swirling cells in a cell culture medium comprising 0.5 to 1.5 µg/ml heparin, 0.5 to 1.5 µM CHIR and 9 to 11 µM ROCK inhibitor.

6. The method according to claim 2, wherein the next four days comprise swirling cells in a cell culture medium comprising 0.5 to 1.5 µg/ml heparin and 0.5 to 1.5 µM CHIR.

7. The method according to claim 2, wherein the next four days comprise culturing cells in a cell culture medium further comprising PVA and MC.

8. The method according to claim 1, wherein the IM cells are swirled between 30 and 90 rpm.

9. The method according to claim 1, wherein the IM cells are swirled for 18 to 24 days.

10. The method according to 1, wherein prior to swirling the population of IM cells, the method further comprises culturing a population of stem cells for at least seven days to produce a population of IM cells, wherein the first 4 to 5 days comprise culturing stem cells in a cell culture medium comprising at least 6 µM of a Wnt/β-catenin agonist and the remaining days in culture comprises culturing cells in a cell culture medium comprising FGF and at least 0.5 µM of a Wnt/β-catenin agonist.

11. The method of claim 10, wherein the Wnt/β-catenin agonist is CHIR, and the FGF is FGF9.

12. The method according to claim 10, wherein the cell culture medium comprising FGF further comprises 0.5 to 1.5 µg/ml heparin.

13. The method according to claim 10, wherein the stem cells are pluripotent stem cells, embryonic stem cells or induced pluripotent stem (iPS) cells.

14. The method according to claim 1, wherein the IM cells are dissociated with EDTA or trypsin and passed through a mesh screen before swirling.

15. The method according to claim 1, which comprises swirling an IM cell population which comprises from $0.5 \times 10^6$ IM cells/ml to $1.5 \times 10^6$ IM cells/ml.

16. The method of claim 1, wherein the kidney organoid has a diameter less than 500 µm.

17. The method of claim 1, wherein the kidney organoid comprises less than 50 nephrons.

* * * * *